(12) United States Patent
Choi et al.

(10) Patent No.: US 10,709,584 B2
(45) Date of Patent: Jul. 14, 2020

(54) ADAPTIVE ROBOTIC FINGER PROSTHESIS FOR GRASPING ARBITRARY OBJECT SHAPE

(71) Applicant: INDUSTRY-UNIVERSITY COOPERATION FOUNDATION HANYANG UNIVERSITY ERICA CAMPUS, Ansan-si, Gyeonggi-do (KR)

(72) Inventors: Youngjin Choi, Seongnam-si (KR); Dukchan Yoon, Guri-si (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 146 days.

(21) Appl. No.: 15/957,407

(22) Filed: Apr. 19, 2018

(65) Prior Publication Data
US 2018/0235782 A1    Aug. 23, 2018

Related U.S. Application Data

(63) Continuation of application No. PCT/KR2016/011485, filed on Oct. 13, 2016.

(30) Foreign Application Priority Data

Oct. 19, 2015  (KR) .................. 10-2015-0145283
Aug. 4, 2016   (KR) .................. 10-2016-0099230

(51) Int. Cl.
*A61F 2/58*    (2006.01)
*A61F 2/68*    (2006.01)
(Continued)

(52) U.S. Cl.
CPC ............... *A61F 2/68* (2013.01); *A61F 2/586* (2013.01); *B25J 15/08* (2013.01);
(Continued)

(58) Field of Classification Search
CPC .... A61F 2/58; A61F 2/586; A61F 2/68; A61F 2002/7862
See application file for complete search history.

(56) References Cited

U.S. PATENT DOCUMENTS 5,762,390 A * 6/1998 Gosselin .............. B25J 15/0009
                                              294/106
6,908,489 B2 * 6/2005 Didrick ................... A61F 2/586
                                              623/64

(Continued)

FOREIGN PATENT DOCUMENTS

JP    2016-068192 A     5/2016
KR    10-2006-0123058 A   12/2006
(Continued)

OTHER PUBLICATIONS

International Search Report of PCT/KR2016/011485 dated Jan. 24, 2017.

*Primary Examiner* — Bruce E Snow
(74) *Attorney, Agent, or Firm* — Sughrue Mion, PLLC

(57) ABSTRACT

An adaptive robotic finger prosthesis according to the inventive concepts includes a proximal phalanx body configured to be worn on a proximal phalanx portion of a cut finger, a middle phalanx body connected to the proximal phalanx body and configured to function as a middle phalanx portion of the cut finger, a distal phalanx body connected to the middle phalanx body and configured to function as a distal phalanx portion of the cut finger, a first proximal phalanx link disposed under the proximal phalanx body, a second proximal phalanx link disposed on the proximal phalanx body and joint-connected to the first proximal phalanx link, and a proximal phalanx elastic member provided at a joint between the first proximal phalanx link and the second proximal phalanx link to provide elastic force.

12 Claims, 18 Drawing Sheets

(51) Int. Cl.
*B25J 15/08* (2006.01)
*A61F 2/50* (2006.01)
*A61F 2/70* (2006.01)
*A61F 2/78* (2006.01)

(52) U.S. Cl.
CPC .......... *A61F 2002/5007* (2013.01); *A61F 2002/5043* (2013.01); *A61F 2002/704* (2013.01); *A61F 2002/7862* (2013.01)

(56) References Cited

U.S. PATENT DOCUMENTS

| | | |
|---|---|---|
| 8,562,049 B2 | 10/2013 | Ihrke et al. |
| 2011/0144770 A1* | 6/2011 | Moyer .................... A61F 2/586 623/64 |
| 2014/0191522 A1* | 7/2014 | Birglen ................ B25J 15/0009 294/106 |
| 2018/0235782 A1* | 8/2018 | Choi ........................ B25J 15/08 |

FOREIGN PATENT DOCUMENTS

| | | |
|---|---|---|
| KR | 10-2010-0022877 A | 3/2010 |
| KR | 10-2011-0109472 A | 10/2011 |
| KR | 10-2011-0111871 A | 10/2011 |
| KR | 10-2014-0109688 A | 9/2014 |
| KR | 10-2015-0144084 A | 12/2015 |

\* cited by examiner

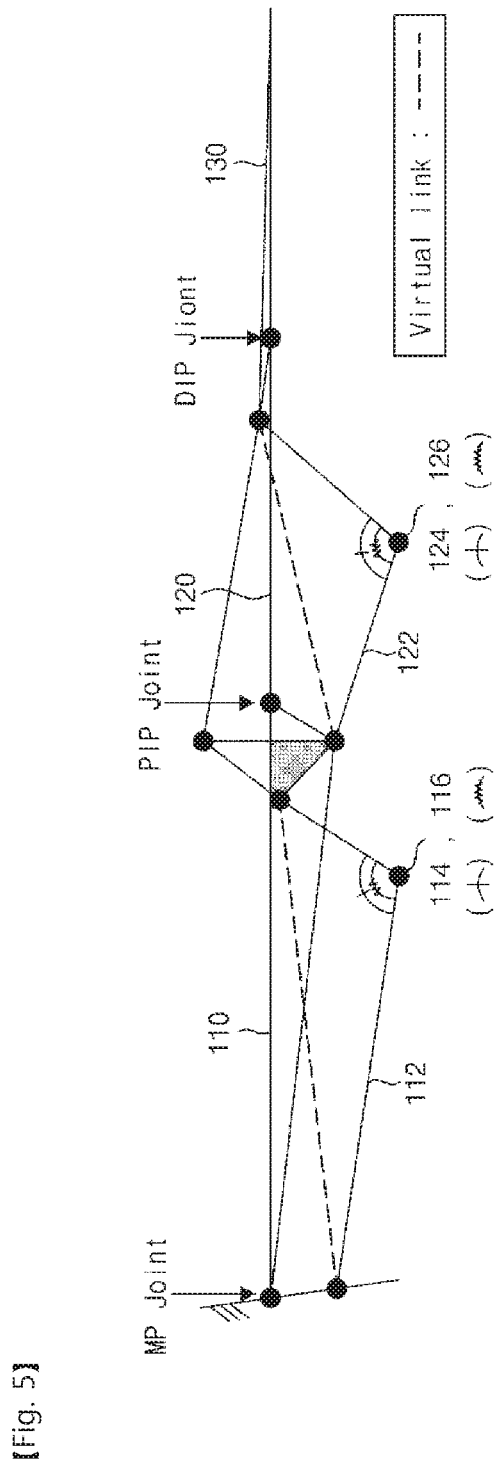

[Fig. 6]
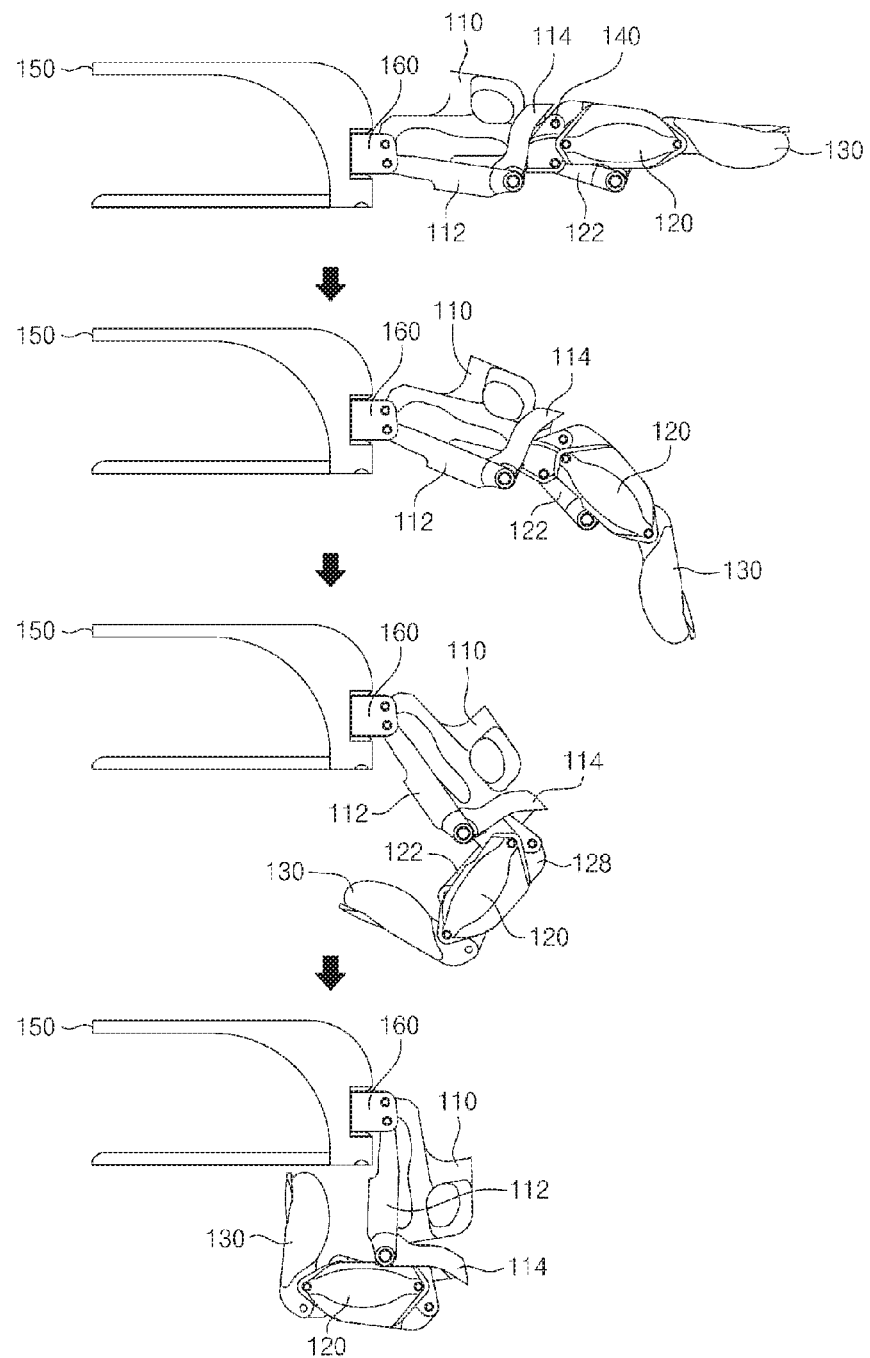

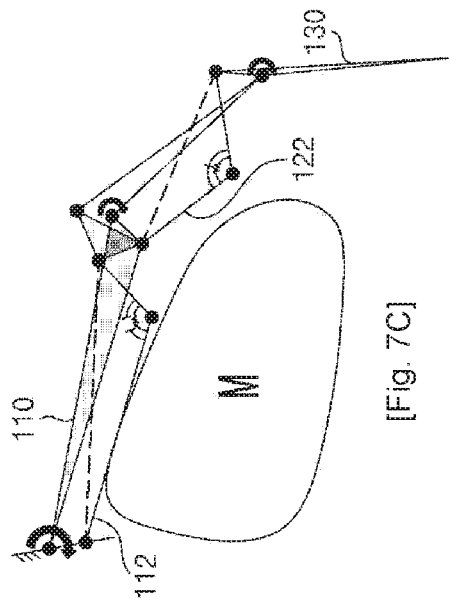
[Fig. 7A]
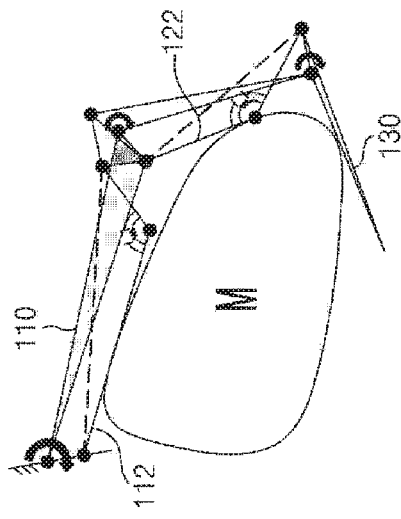
[Fig. 7B]
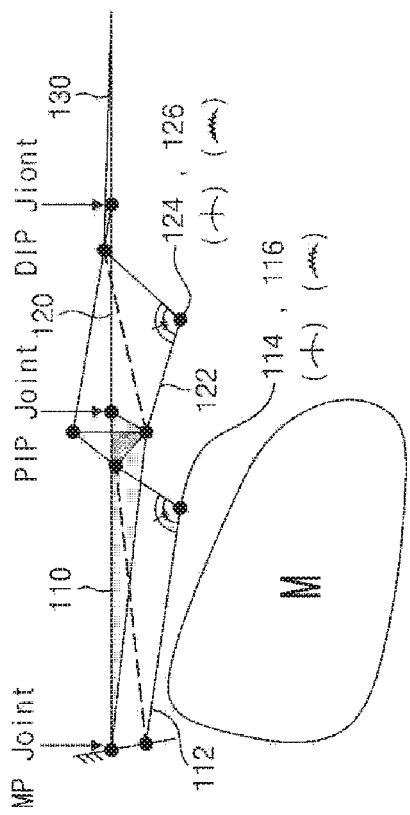
[Fig. 7C]
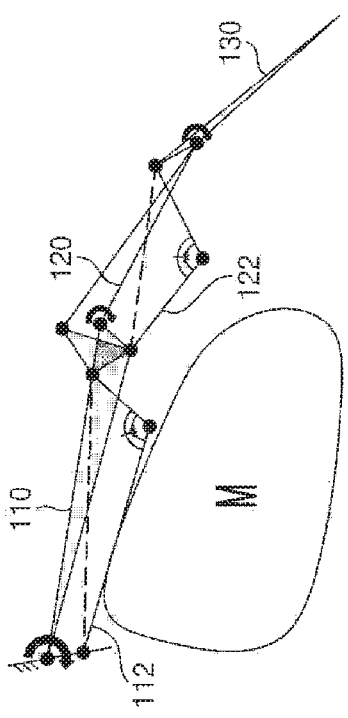
[Fig. 7D]

[Fig. 8]
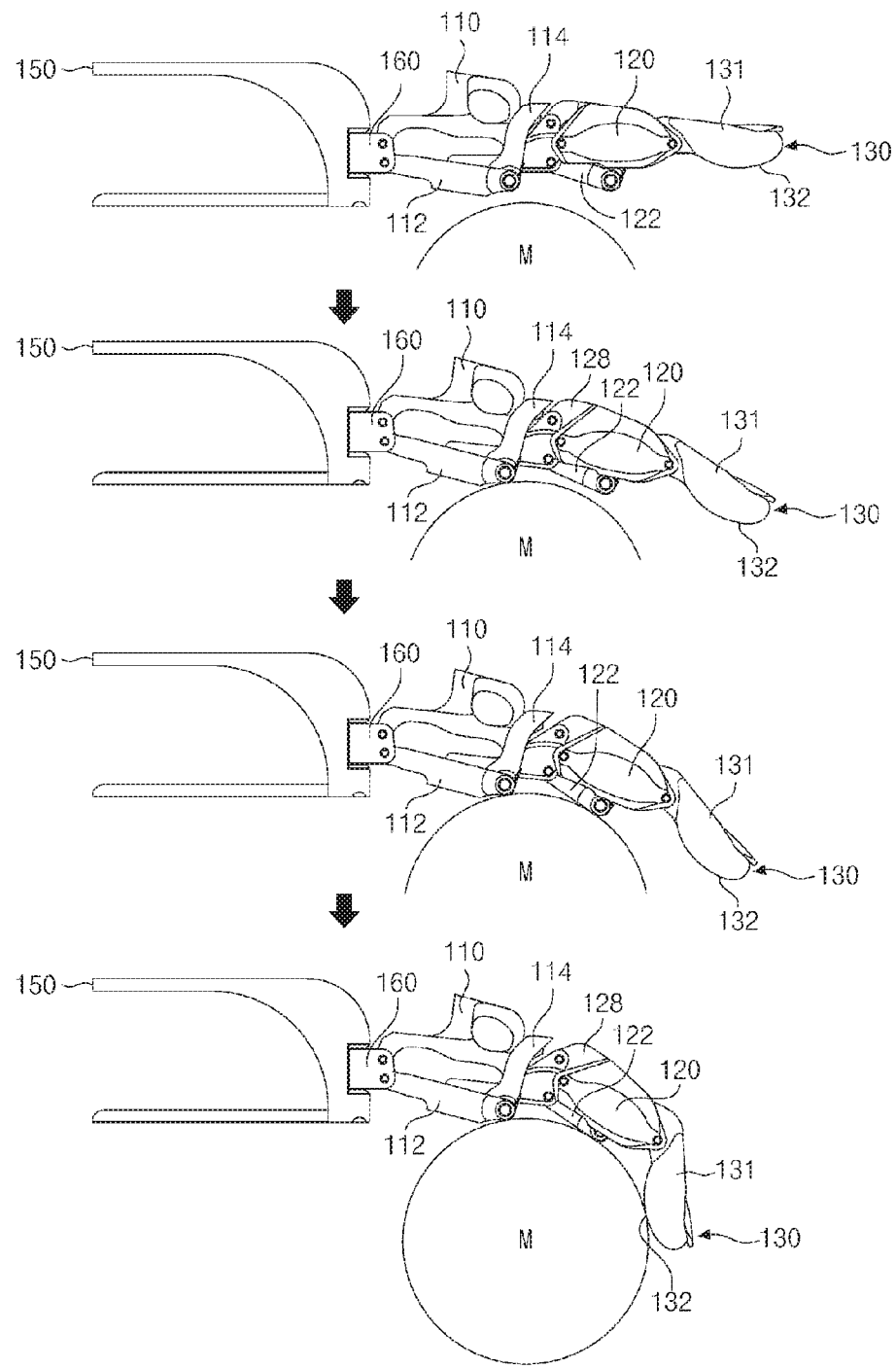

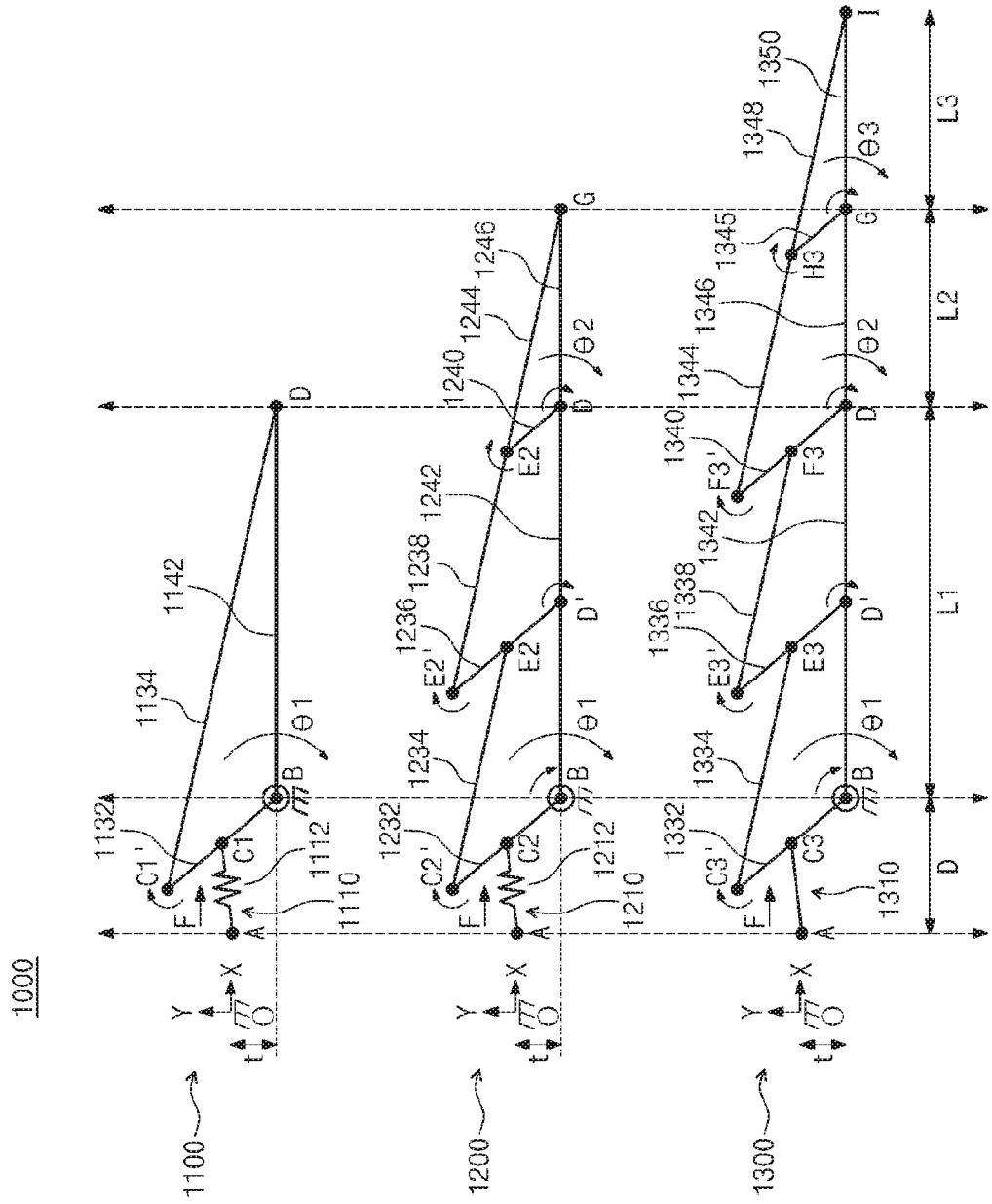

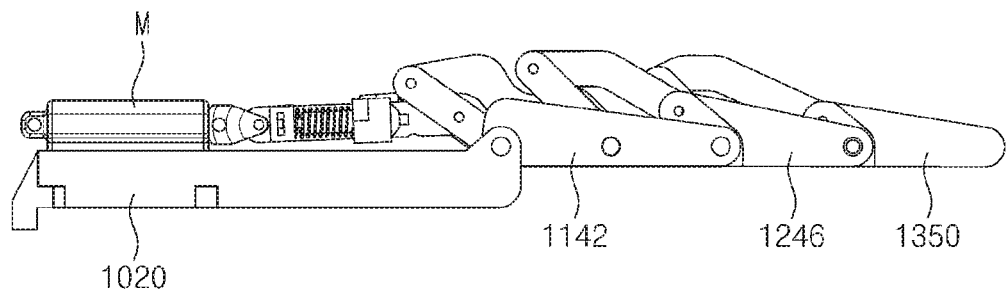
[Fig. 10A]
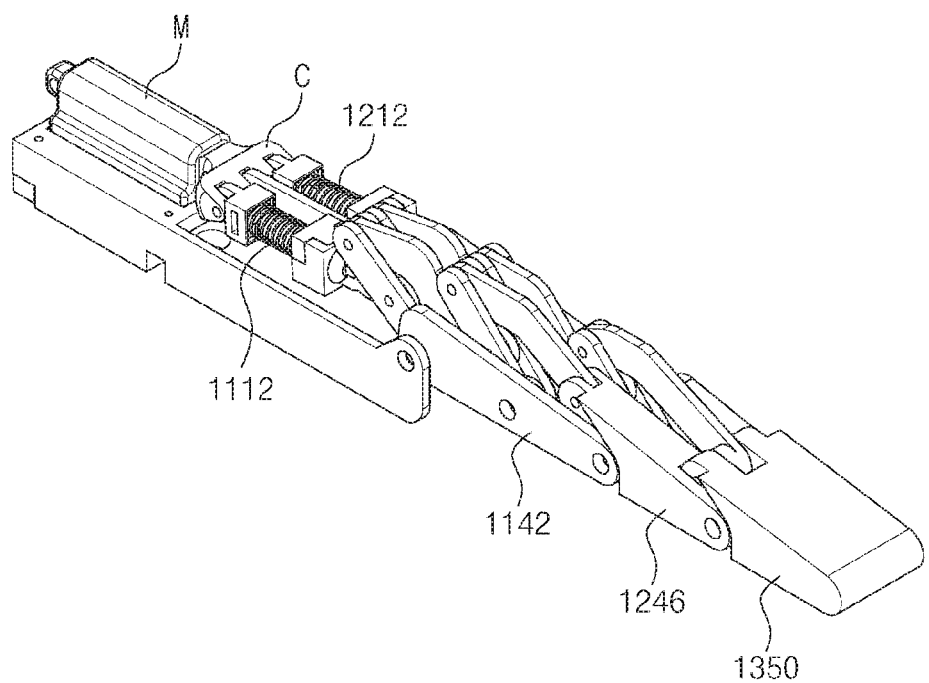
[Fig. 10B]

[Fig. 11]
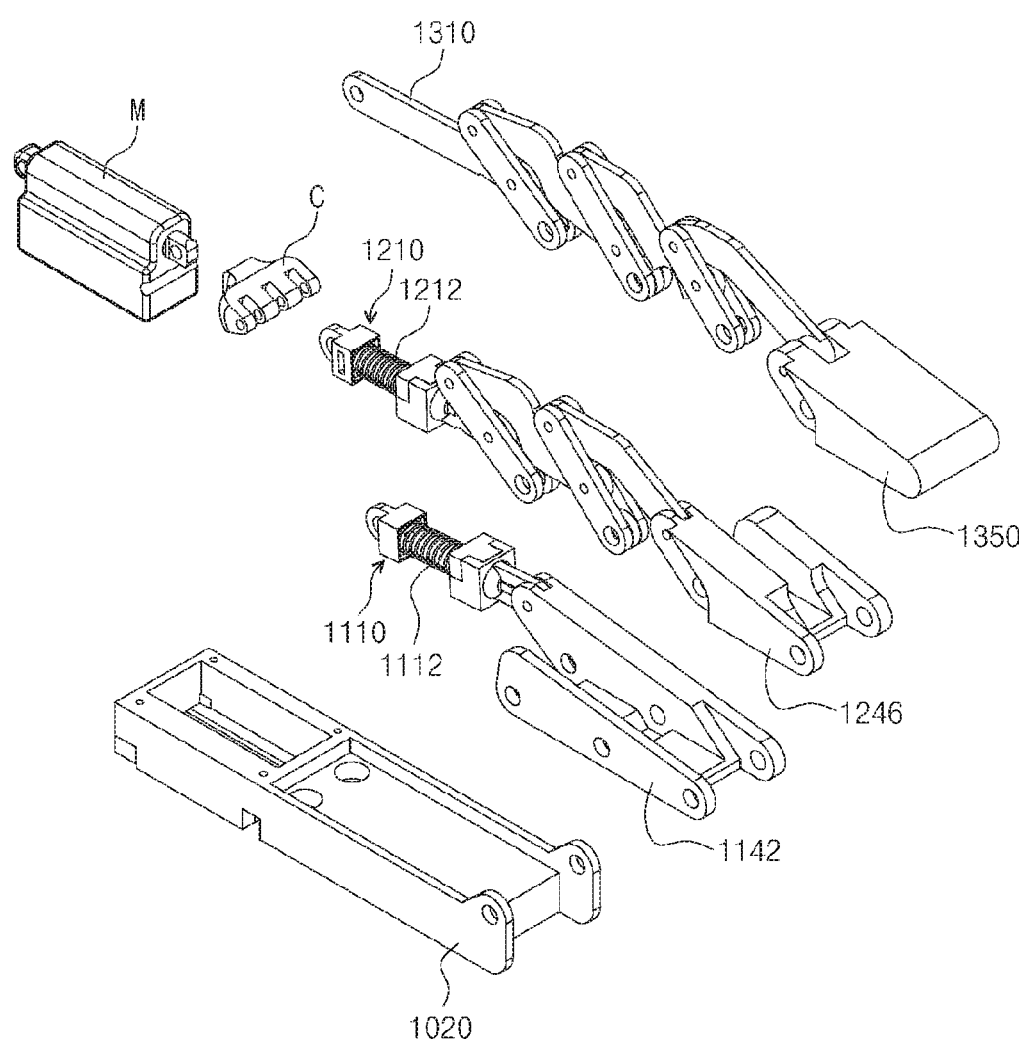

[Fig. 12]
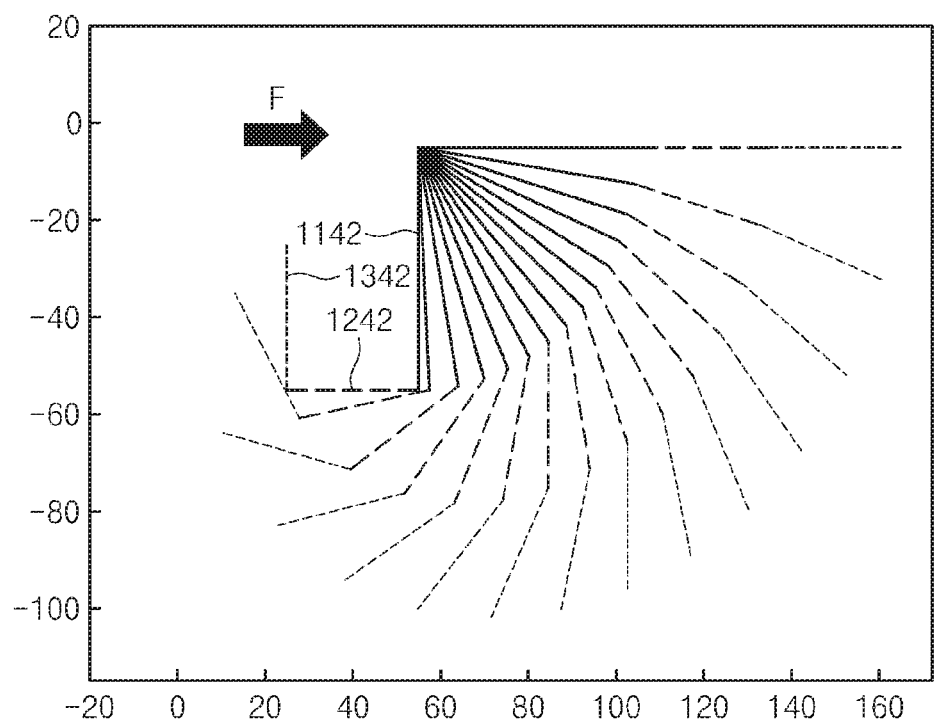
[Fig. 13]
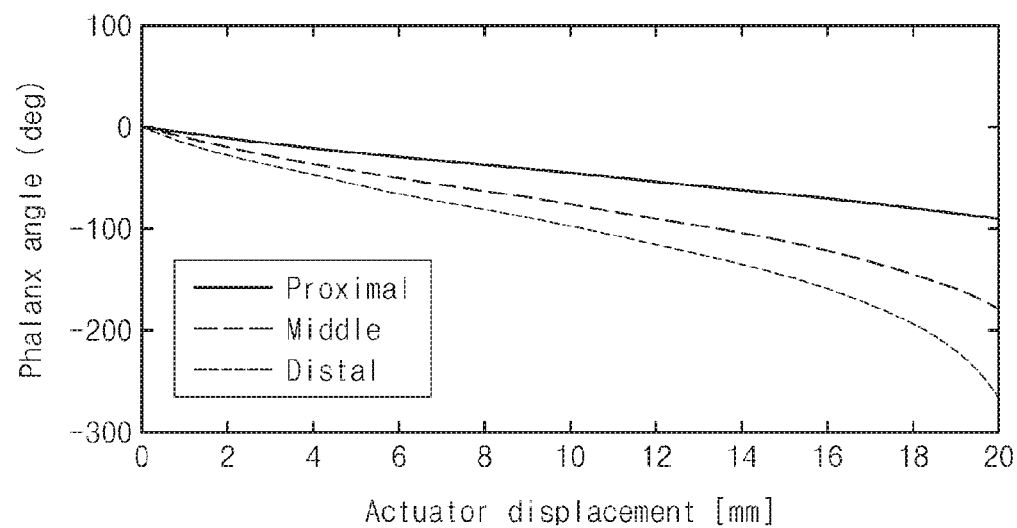

[Fig. 14]
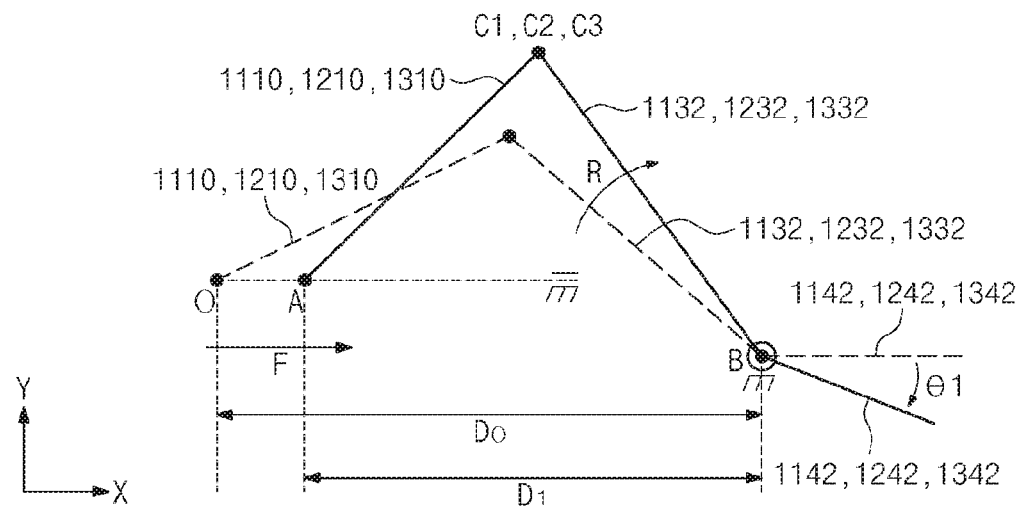
[Fig. 15]
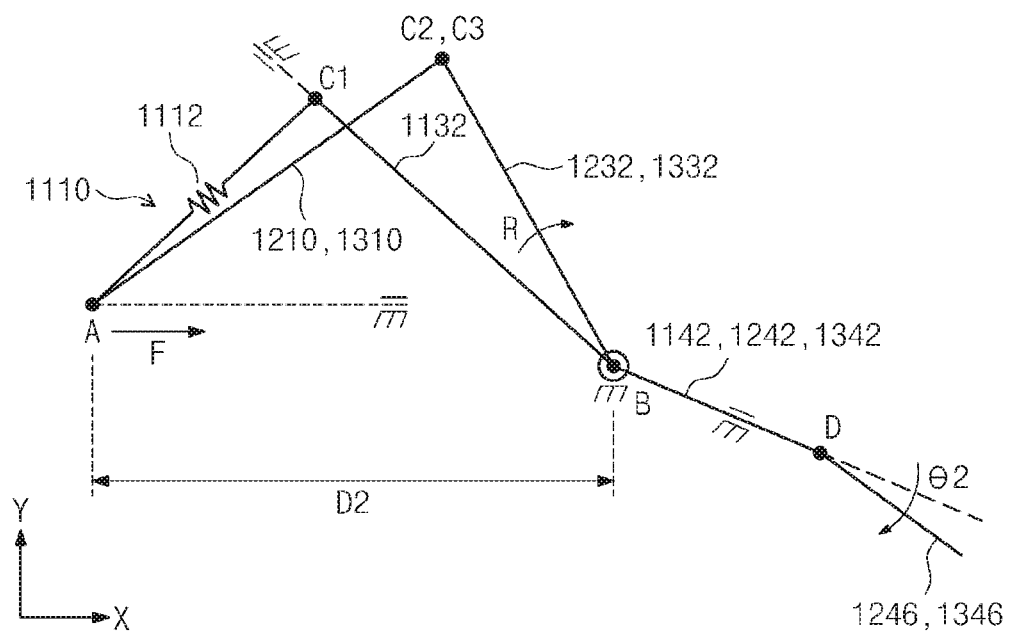

[Fig. 16]
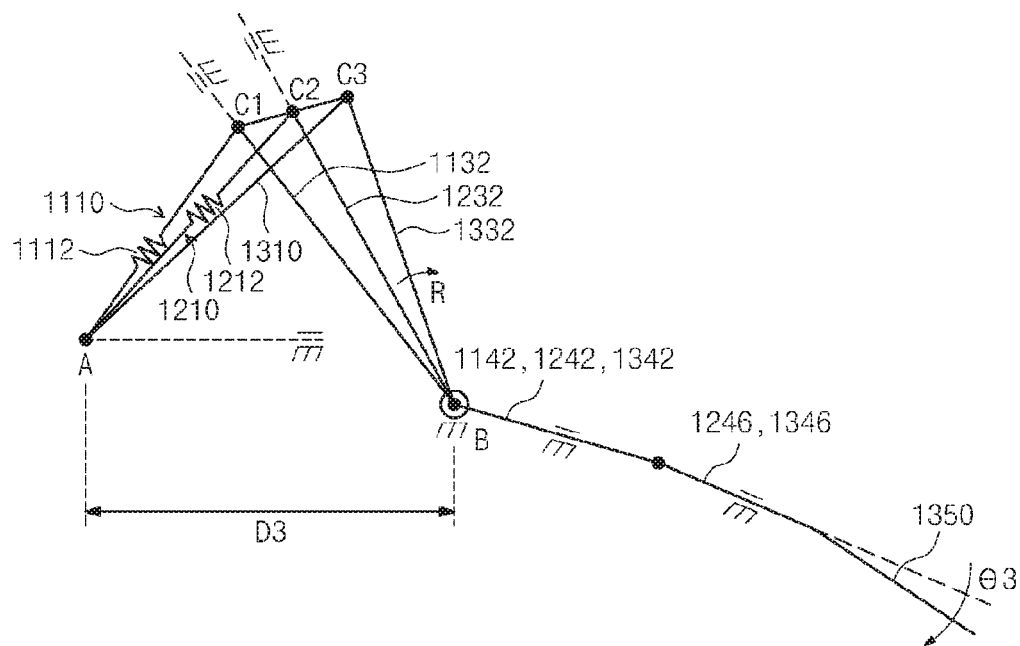
[Fig. 17]
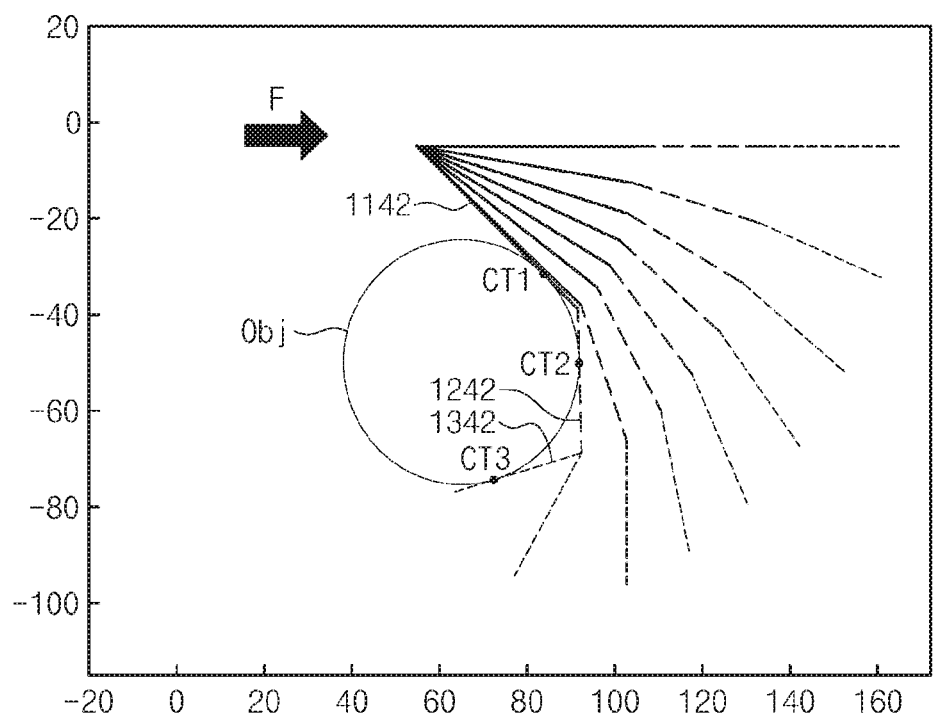

[Fig. 18]
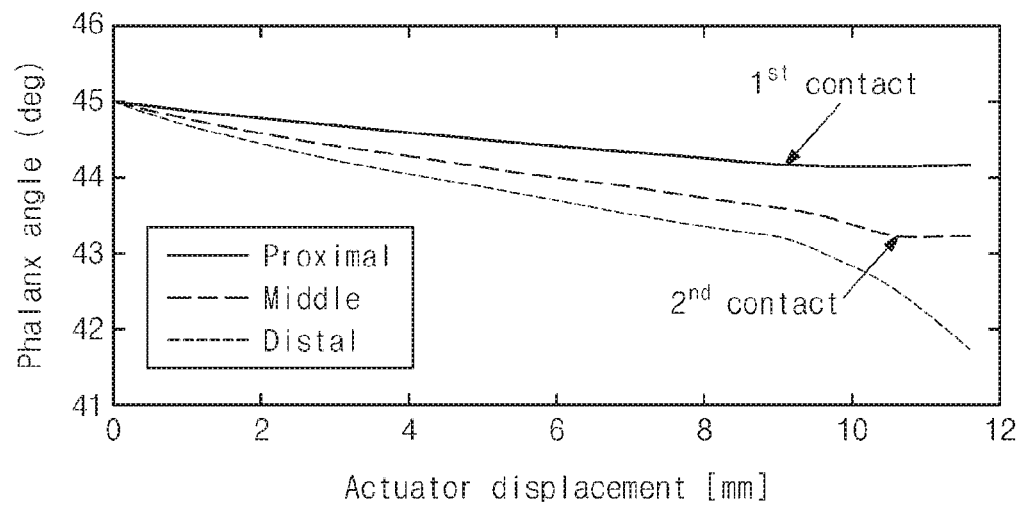
[Fig. 19]
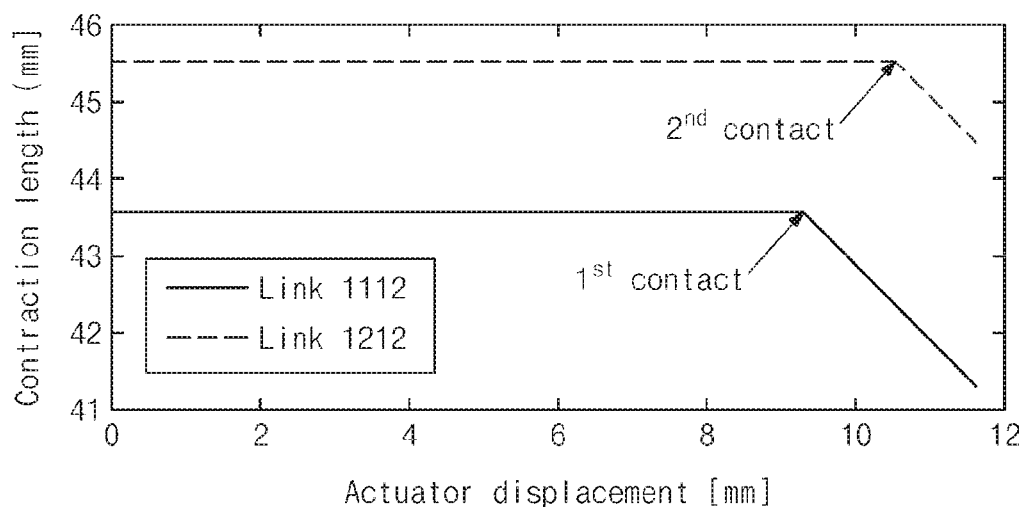

[Fig. 20]
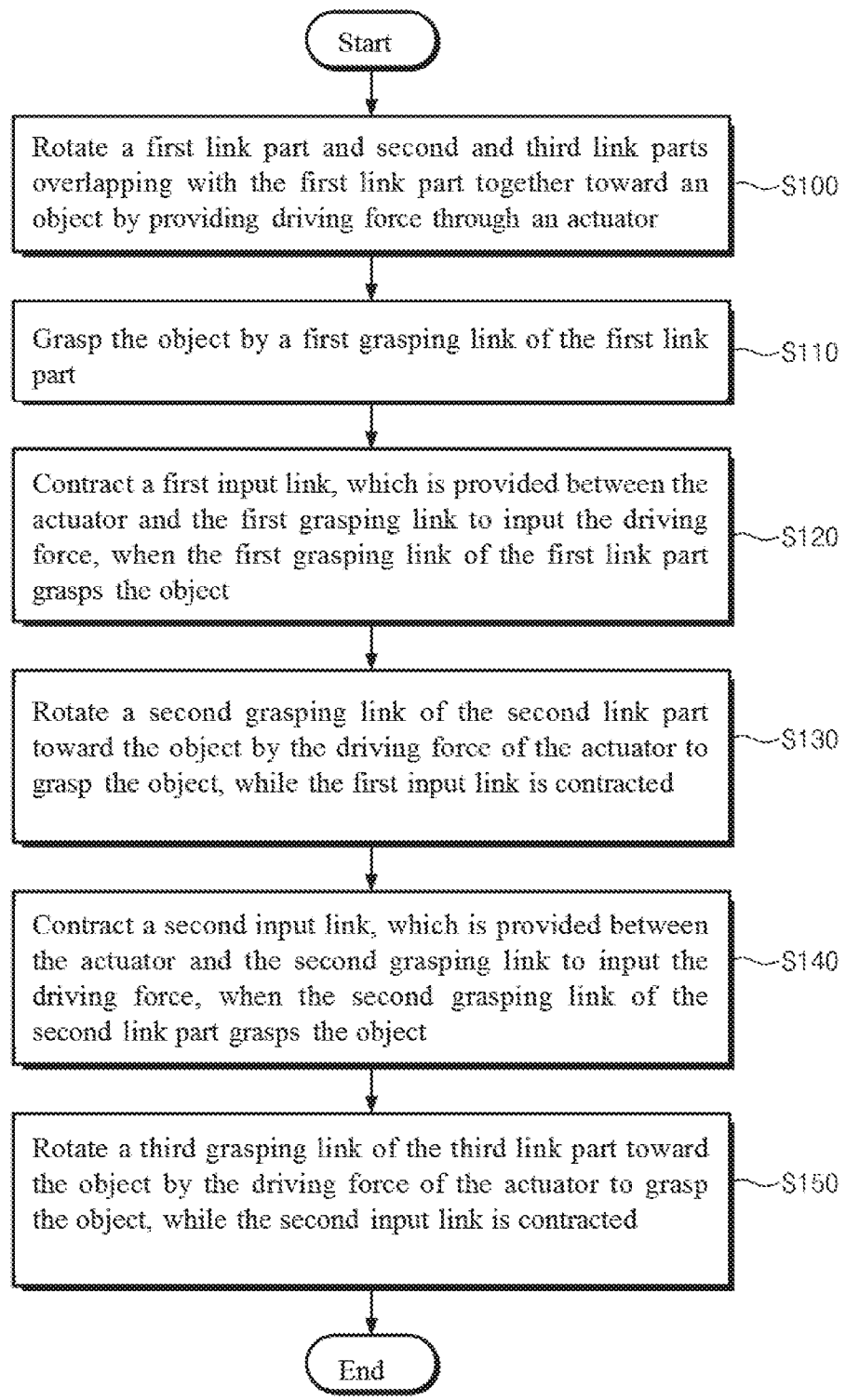

[Fig. 21]
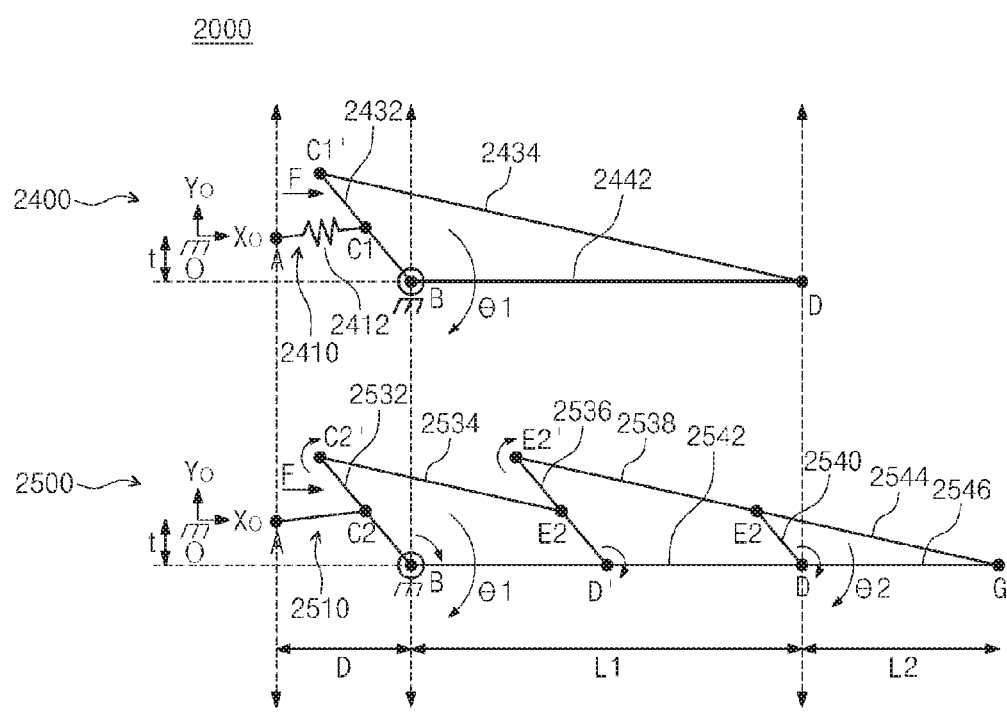

[Fig. 22]
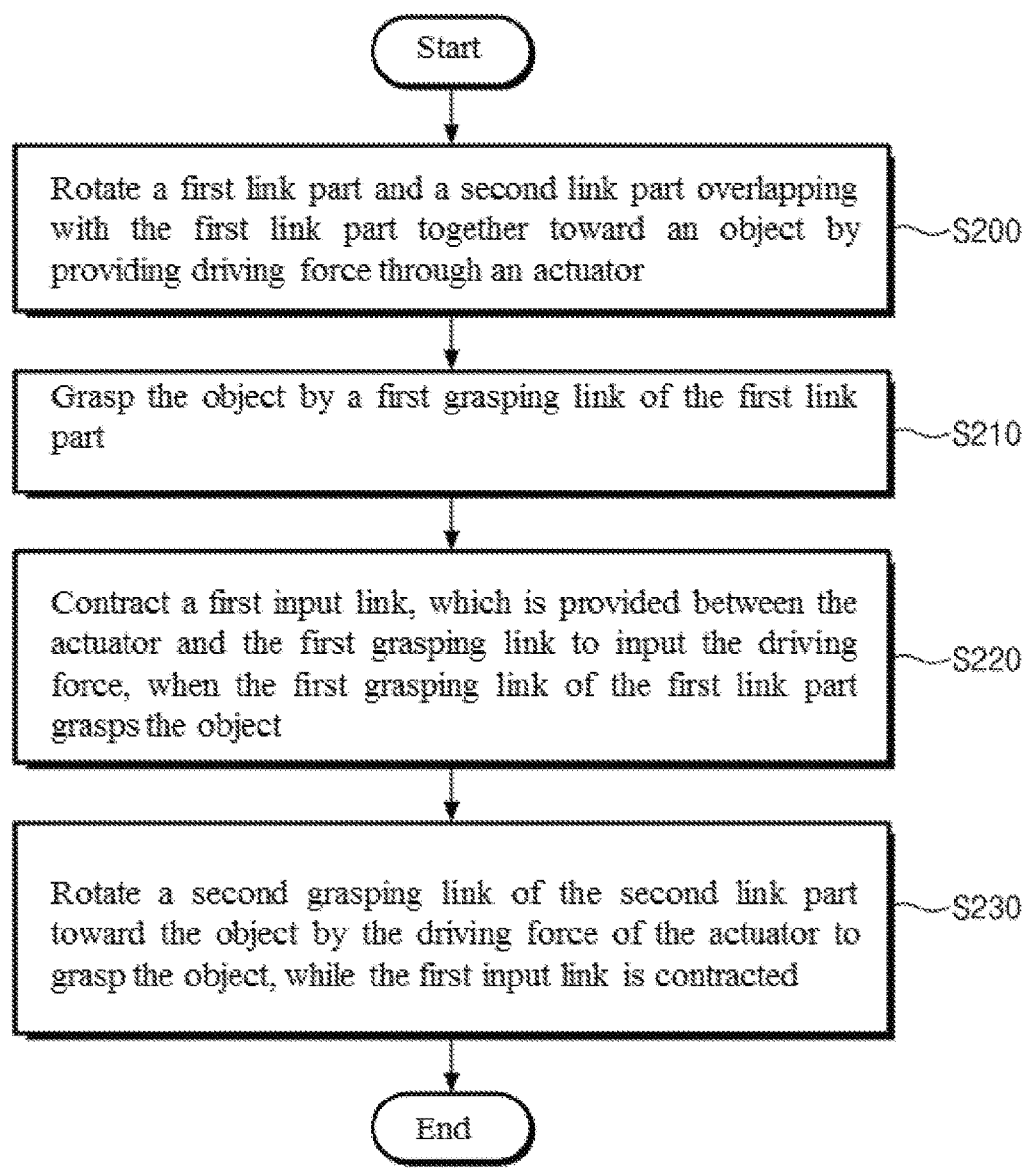

ADAPTIVE ROBOTIC FINGER PROSTHESIS FOR GRASPING ARBITRARY OBJECT SHAPE

CROSS-REFERENCE TO RELATED APPLICATION

This application is a continuation of pending International Application No. PCT/KR2016/011485, which was filed on Oct. 13, 2016 and claims priority to Korean Patent Application Nos. 10-2015-0145283 and 10-2016-0099230, filed on Oct. 19, 2015 and Aug. 4, 2016, in the Korean Intellectual Property Office, the disclosures of which are hereby incorporated by reference in their entireties.

BACKGROUND

1. Field

The present disclosure relates to an adaptive robotic finger prosthesis for grasping an arbitrary object shape. More particularly, the present disclosure relates to an adaptive robotic finger prosthesis for grasping an arbitrary object shape, which is capable of performing a finger grasping motion, a finger bending motion, and a finger stretching motion without a separate actuator by a user of which a portion of a finger is cut.

2. Description of the Related Art

Generally, when a patient having a cut finger has an enough proximal phalanx (i.e., a first phalanx) of the cut finger and can move the proximal phalanx, a robotic finger prosthesis is mounted on the proximal phalanx and the patient moves the robotic finger prosthesis himself or herself. In other words, the robotic finger prosthesis is a device that is mounted on the cut finger to allow the patient to perform a grasping motion and a bending or stretching motion when the patient moves the cut finger himself or herself.

These typical robotic finger prostheses may be mainly classified into four types. An X-finger of Didrick medical Inc. has been developed and marketed commercially. A LARM robotic finger of performing the same motion as the X-finger has been developed by Cassino university of Italy. In addition, an object-adaptive robotic finger of Cassino university of Italy and a robotic hand of Tsinghua university of China have been to overcome disadvantages of the LARM robotic finger.

In more detail, Didrick medical Inc. developed the X-finger corresponding to an artificial finger composed of a 4-bar link operated using a joint and a bar of a proximal phalanx remaining after a finger was cut, not using an external actuator, and Cassino university of Italy also developed a finger mechanism similar thereto.

However, the X-finger of Didrick medical Inc. and the LARM finger mechanism of Cassino university of Italy are an under-actuated system having one degree of freedom. Since motions of joints and bars of a middle phalanx and a distal phalanx are dependent on motions of the joint and the bar of the proximal phalanx in the X-finger and the LARM finger mechanism, a bending or stretching motion of the finger may be performed without difficulty. However, when the X-finger and the LARM finger grasp variously shaped objects, motions of the X-finger and the LARM finger are stopped in states in which the X-finger and the LARM finger are initially in contact with the objects, and the joints and bars of the middle phalanx and the distal phalanx having chain motions are also stopped. In other words, in the X-finger and the LARM finger mechanism, an end of the finger may be separated from an object, and thus ability to grasp an object may be unstable.

To solve these problems of the X-finger and the LARM finger mechanism, the object-adaptive robotic finger mechanism has been developed in Cassino university of Italy on the basis of the LARM finger mechanism. In the object-adaptive robotic finger mechanism, a spring and a crank slider were applied to the LARM finger mechanism. The robotic finger mechanism of Tsinghua university of China uses a new method in which a joint of a finger is bent by using a spring and a slide link when an object comes in contact with a bottom of a finger and applies external force to the finger.

However, since the typical object-adaptive finger mechanism cannot perform a bending or stretching motion of a human actual finger, it only has a meaning as a gripper corresponding to an end device of a manipulator. In other words, the typical object-adaptive robotic finger is not bent when it does not come in contact with an object, and thus motions thereof are not different from those of a human actual finger.

Cassino university of Italy suggested a method for solving the problems of the object-adaptive finger mechanism and the LARM finger mechanism. In the method, one link is added to a LARM finger mechanism based on a 4-bar link to change the 4-bar link into a 5-bar link, and a spring is connected between two links to perform motions in the form of the 4-bar link in bending and stretching motions. In addition, when an object comes in contact with an artificial finger, an actuator is continuously operated to increase an angle between the two links between which the spring is connected, and thus second and third bars of the artificial finger are rotated.

However, in the 5-bar link LARM finger mechanism, the artificial finger is operated using a first end of the link in the finger to which the spring is installed, and thus a motor should be continuously operated in the state in which an object comes in contact with the artificial finger. Accordingly, the 5-bar link LARM finger mechanism is not suitable for an artificial finger that transfers power by using a remaining phalanx of a finger, not an external motor.

Therefore, embodiments of the inventive concepts are suggested to overcome the above problems. Meanwhile, Korean Patent Publication No. 10-2011-003285 (published on Mar. 30, 2011) discloses a finger rehabilitation exerciser.

SUMMARY

Embodiments of the inventive concepts may provide an adaptive robotic finger prosthesis for grasping an arbitrary object shape, which is capable of performing a pinch motion of bending and stretching and a motion of grasping various-shaped objects by using a remaining proximal phalanx portion of a finger without a separate actuator.

Embodiments of the inventive concepts may also provide a robotic driving mechanism capable of performing bending, stretching and grasping motions and a method of driving the same.

Embodiments of the inventive concepts may further provide a robotic driving mechanism operated with under-actuation and a method of driving the same.

Embodiments of the inventive concepts may further provide a robotic driving mechanism that adapts to a shape of an object to stably grasp various-shaped objects, and a method of driving the same.

In an aspect, an adaptive robotic finger prosthesis may include a proximal phalanx body configured to be worn on a proximal phalanx portion of a cut finger, a middle phalanx body connected to the proximal phalanx body and configured to function as a middle phalanx portion of the cut finger, a distal phalanx body connected to the middle phalanx body and configured to function as a distal phalanx portion of the cut finger, a first proximal phalanx link disposed under the proximal phalanx body, a second proximal phalanx link disposed on the proximal phalanx body and joint-connected to the first proximal phalanx link, and a proximal phalanx elastic member provided at a joint between the first proximal phalanx link and the second proximal phalanx link to provide elastic force.

In an embodiment, an angle between the first proximal phalanx link and the second proximal phalanx link may increase as the first proximal phalanx link comes in contact with an object and is pressed, in a motion of grasping the object.

In an embodiment, the second proximal phalanx link may apply force to the middle phalanx body to fold the middle phalanx body and the distal phalanx body inward as the first proximal phalanx link comes in contact with an object and is pressed, in a motion of grasping the object.

In an embodiment, an angle between the first proximal phalanx link and the second proximal phalanx link may be fixed by the proximal phalanx elastic member in a bending or stretching motion performed in the absence of contact with an object.

In an embodiment, a mechanical angle limiting element for limiting the angle between the first and second proximal phalanx links may be provided at one of the first proximal phalanx link and the second proximal phalanx link, such that the angle between the first and second proximal phalanx links may be fixed to an angle of the mechanical angle limiting element by the proximal phalanx elastic member in the bending or stretching motion.

In an embodiment, the adaptive robotic finger prosthesis may further include a first middle phalanx link which is disposed under the middle phalanx body and of which one end portion is joint-connected to the proximal phalanx body, a second middle phalanx link of which one end portion is joint-connected to another end portion of the first middle phalanx link and of which another end portion is joint-connected to the distal phalanx body, a third middle phalanx link which is disposed on the middle phalanx body and which interconnects the proximal phalanx body and the distal phalanx body, and a middle phalanx elastic member provided at a joint between the first and second middle phalanx links to provide elastic force.

In an embodiment, an angle between the first middle phalanx link and the second middle phalanx link may increase as the first middle phalanx link comes in contact with an object and is pressed, in a motion of grasping the object.

In an embodiment, the second middle phalanx link may apply force to the distal phalanx body to fold the distal phalanx body inward as the first middle phalanx link comes in contact with an object and is pressed, in a motion of grasping the object.

In an embodiment, an angle between the first middle phalanx link and the second middle phalanx link may be fixed by the middle phalanx elastic member in a bending or stretching motion performed in the absence of contact with an object.

In an embodiment, a mechanical angle limiting element for limiting the angle between the first and second middle phalanx links may be provided at one of the first middle phalanx link and the second middle phalanx link, such that the angle between the first and second middle phalanx links may be fixed to an angle of the mechanical angle limiting element by the middle phalanx elastic member in the bending or stretching motion.

In an embodiment, the adaptive robotic finger prosthesis may further include a palm fixing part configured to be fixed at a palm of a user. The palm fixing part may be joint-connected to each of the proximal phalanx body and the first proximal phalanx link.

In an embodiment, the adaptive robotic finger prosthesis may further include a connection bracket which joint-connects the palm fixing part to the proximal phalanx body or the first proximal phalanx link. The palm fixing part may be configured to be rotated inward and outward with respect to the proximal phalanx body or the first proximal phalanx link by the connection bracket.

In another aspect, an adaptive robotic finger prosthesis for grasping an arbitrary object shape may be worn on a proximal phalanx portion of a cut finger to use the proximal phalanx portion as power. The adaptive robotic finger prosthesis may be based on a 5-bar link structure. A 4-bar link involved in a bending or stretching motion performed in the absence of contact with an object may be formed differently from a 4-bar link involved in a grasping motion of the object, in the adaptive robotic finger prosthesis. The two motions may be performed at the same time or may be performed independently of each other.

In an embodiment, a joint elastic member and a mechanical angle limiting element may be provided between a first link coming in contact with the object and a second link joint-connected to the first link in the 5-bar link structure.

In an embodiment, an angle between the first link and the second link may increase by external force generated by bringing the first link into contact with the object, in the grasping motion of the object, and the angle between the first link and the second link may be fixed to an angle of the mechanical angle limiting element by the joint elastic member in the bending or stretching motion.

BRIEF DESCRIPTION OF THE DRAWINGS

FIG. 5 is a schematic view illustrating mechanism of bending and stretching motions of the adaptive robotic finger prosthesis of FIG. 1.

FIG. 6 is a schematic view illustrating the bending and stretching motions according to the motion mechanism of the adaptive robotic finger prosthesis illustrated in FIG. 5.

FIGS. 7A-7D illustrate mechanism of a grasping motion of the adaptive robotic finger prosthesis of FIG. 1.

FIG. 8 is a schematic view illustrating the grasping motion according to the motion mechanism of the adaptive robotic finger prosthesis illustrated in FIGS. 7A-7D.

FIG. 9 is a schematic view illustrating a link of a robotic driving mechanism according to a first embodiment of the inventive concepts.

FIGS. 10A and 10B illustrate a cross-sectional view and a perspective view of the robotic driving mechanism according to the first embodiment of the inventive concepts.

FIG. 11 is an exploded perspective view illustrating the robotic driving mechanism according to the first embodiment of the inventive concepts.

FIGS. 12 and 13 show experimental results of bending and stretching motions of the robotic driving mechanism according to the first embodiment of the inventive concepts.

FIGS. 14 to 16 are schematic views illustrating a grasping motion of the robotic driving mechanism according to the first embodiment of the inventive concepts.

FIGS. 17 to 19 show experimental results of the grasping motion of the robotic driving mechanism according to the first embodiment of the inventive concepts.

FIG. 20 is a flowchart illustrating a method of driving the robotic driving mechanism according to the first embodiment of the inventive concepts.

FIG. 21 is a schematic view illustrating a link of a robotic driving mechanism according to a second embodiment of the inventive concepts.

FIG. 22 is a flowchart illustrating a method of driving the robotic driving mechanism according to the second embodiment of the inventive concepts.

DETAILED DESCRIPTION OF THE EMBODIMENTS

Figure 1:
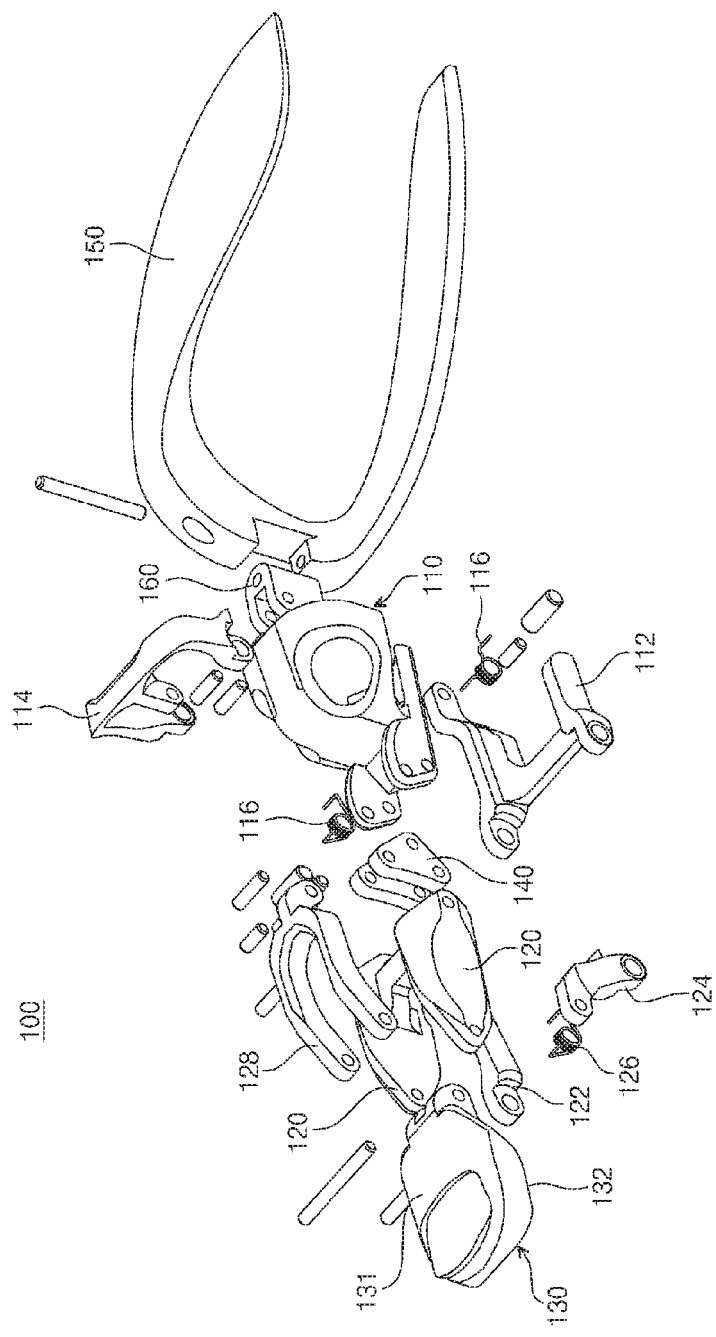
FIG. 1 is an exploded perspective view illustrating an adaptive robotic finger prosthesis for grasping an arbitrary object shape, according to an embodiment of the inventive concepts.

The inventive concepts will now be described more fully hereinafter with reference to the accompanying drawings, in which exemplary embodiments of the inventive concepts are shown. It should be noted, however, that the inventive concepts are not limited to the following exemplary embodiments, and may be implemented in various forms. Accordingly, the exemplary embodiments are provided only to disclose the inventive concepts and let those skilled in the art know the category of the inventive concepts.

Exemplary embodiments are described herein with reference to cross-sectional illustrations and/or plane illustrations that are idealized exemplary illustrations. In the drawings, the sizes and ratios of components are exaggerated for clarity. The same reference numerals or the same reference designators denote the same elements throughout the specification.

Accordingly, variations from the shapes of the illustrations as a result, for example, of manufacturing techniques and/or tolerances, are to be expected. Thus, exemplary embodiments should not be construed as limited to the shapes of regions illustrated herein but are to include deviations in shapes that result, for example, from manufacturing.

An adaptive robotic finger prosthesis 100 for grasping an arbitrary object shape (hereinafter, referred to as 'a robotic finger prosthesis 100') according to an embodiment of the inventive concepts will be described hereinafter with reference to the accompanying drawings.

Figure 2:
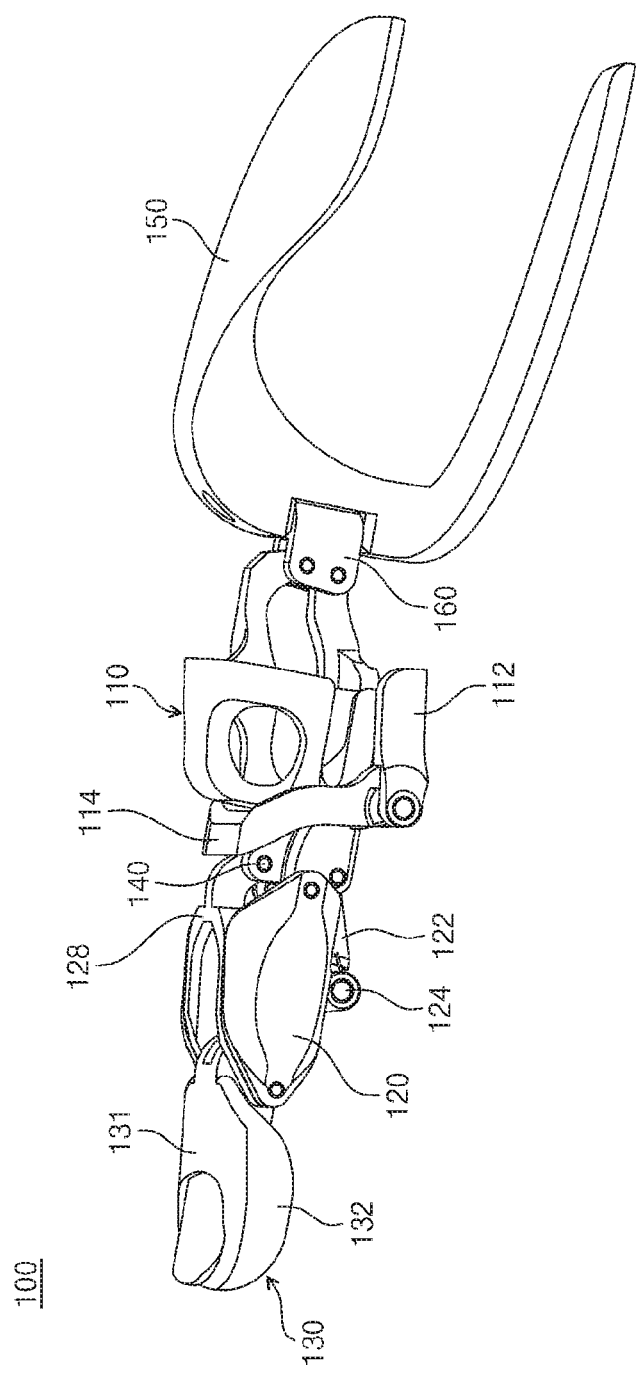
FIG. 2 is a perspective view illustrating the adaptive robotic finger prosthesis of FIG. 1.
Figure 3:
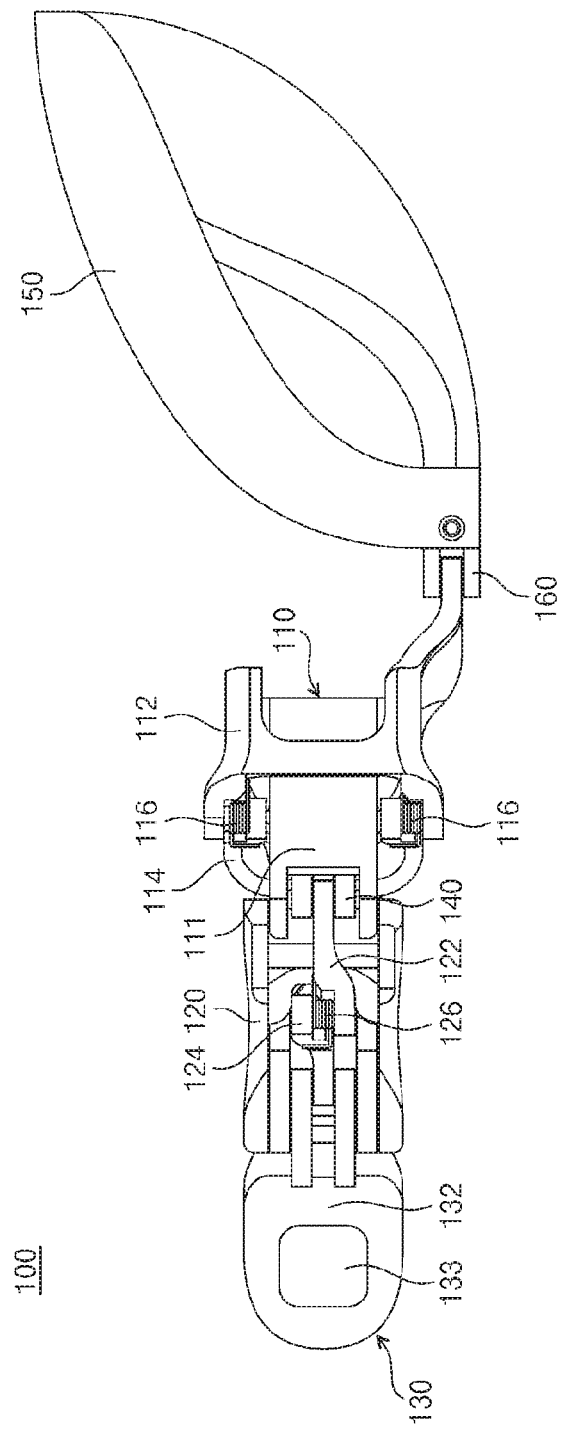
FIG. 3 is a bottom view illustrating the adaptive robotic finger prosthesis of FIG. 1.
Figure 4:
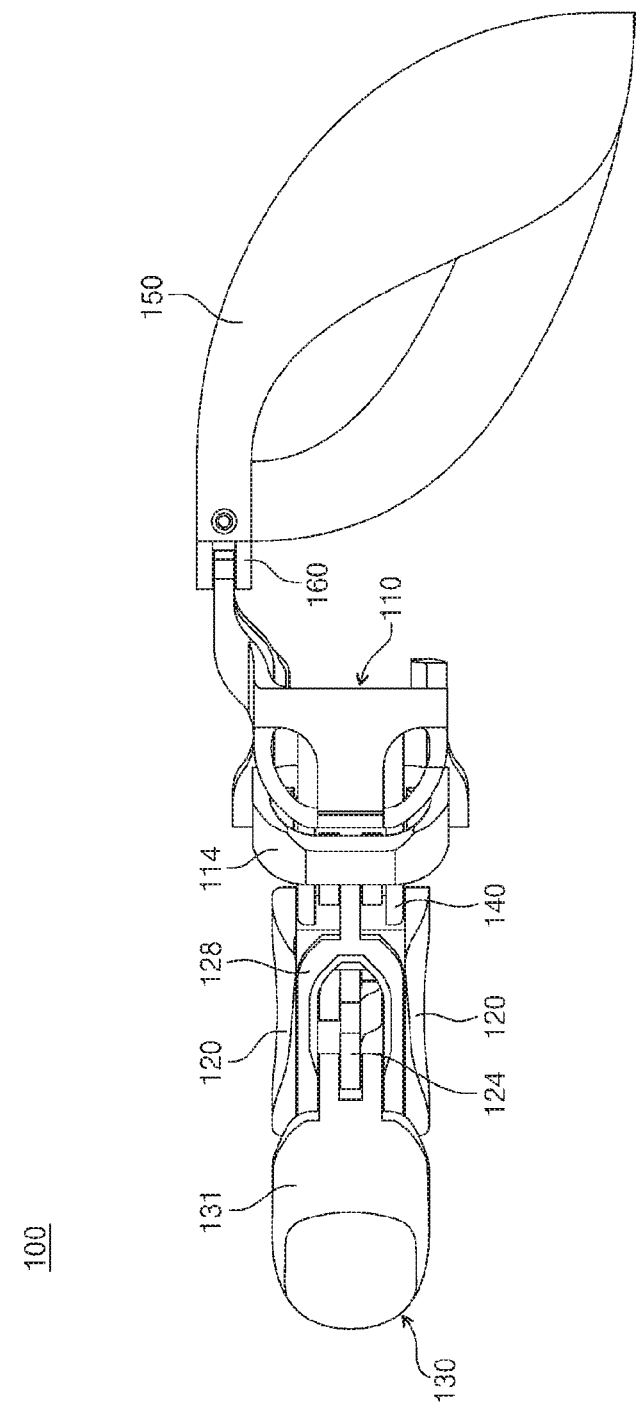
FIG. 4 is a top view illustrating the adaptive robotic finger prosthesis of FIG. 1.

FIG. 1 is an exploded perspective view illustrating an adaptive robotic finger prosthesis for grasping an arbitrary object shape, according to an embodiment of the inventive concepts, and FIG. 2 is a perspective view illustrating the adaptive robotic finger prosthesis of FIG. 1. FIG. 3 is a bottom view illustrating the adaptive robotic finger prosthesis of FIG. 1, and FIG. 4 is a top view illustrating the adaptive robotic finger prosthesis of FIG. 1.

Referring to FIGS. 1 to 4, the robotic finger prosthesis 100 according to an embodiment of the inventive concepts includes a proximal phalanx body 110 configured to be worn or mounted on a proximal phalanx portion of a finger, a middle phalanx body 120 connected to the proximal phalanx body 110 and configured to function as a middle phalanx portion of the finger, a distal phalanx body 130 connected to the middle phalanx body 120 and configured to function as a distal phalanx portion of the finger, a first proximal phalanx link 112 disposed under the proximal phalanx body 110, a second proximal phalanx link 114 disposed on the proximal phalanx body 110, and a proximal phalanx elastic member 116 provided between the first proximal phalanx link 112 and the second proximal phalanx link 114.

The robotic finger prosthesis 100 according to an embodiment of the inventive concepts is provided for a user who has a remaining proximal phalanx portion of a finger and whose middle phalanx and distal phalanx portions of the finger are cut and are removed. In other words, the robotic finger prosthesis 100 is a robotic prosthesis for a user whose a finger is not completely cut but whose a proximal phalanx portion remains. In addition, since the proximal phalanx portion of the finger is fixed to or supported by the proximal phalanx body 110 to provide power (or force) to the robotic finger prosthesis 100, a user having a sufficiently remaining proximal phalanx portion may use the robotic finger prosthesis 100.

As described above, the robotic finger prosthesis 100 is worn or mounted on the proximal phalanx portion of the cut finger and uses power (or force) of the proximal phalanx portion. The robotic finger prosthesis 100 is formed based on a 5-bar link structure. However, in the robotic finger prosthesis 100, a 4-bar link involved in a bending or stretching motion in a state where an object M is not in contact with the robotic finger prosthesis 100 is formed differently from a 4-bar link involved in a grasping motion in a state where an object M is in contact with the robotic finger prosthesis 100. At this time, the robotic finger prosthesis 100 may perform the two motions at the same time or independently of each other. In other words, since the link (e.g., a link inputting the power or force) involved in the bending or stretching motion is different from the link (e.g., a link receiving external force) involved in the grasping motion for picking up an object in the robotic finger prosthesis 100, the robotic finger prosthesis 100 performs the bending or stretching motion and the grasping motion independently of each other. In addition, in the 5-bar link structure of the robotic finger prosthesis 100, an elastic member 116 or 126 and a mechanical angle limiting element are provided at a joint between a first link 112 or 122 coming in contact with an object and a second link 114 or 124 joint-connected to the first link 112 or 122. In other words, in the motion of grasping an object using the robotic finger prosthesis 100, an angle between the first link 112 or 122 and the second link 114 or 124 is increased by external force generated when the first link 112 or 122 comes in contact with an object. In addition, in the bending or stretching motion of the robotic finger prosthesis 100, the angle between the first link 112 or 122 and the second link 114 or 124 is fixed at an angle of the mechanical angle limiting element by the elastic member 116 or 126. As described above, the first link may be provided or prepared as the first proximal phalanx link 112 or a first middle phalanx link 122 to be described later, and the second link may be provided or prepared as the second proximal phalanx link 114 or a second middle phalanx link 124 to be described later.

The robotic finger prosthesis 100 according to the embodiment for realizing the above descriptions will be described hereinafter in more detail.

Referring to FIGS. 1 to 4, the proximal phalanx body 110 is worn or mounted on the proximal phalanx portion of the cut finger and functions as the proximal phalanx portion of the user. The proximal phalanx body 110 may mean a proximal phalanx of the finger, i.e., a first phalanx of the finger. The remaining proximal phalanx portion of the user is located at or in the proximal phalanx body 110. At this time, the proximal phalanx body 110 has a cylindrical shape to stably fix or support the located proximal phalanx portion of the user. In addition, a bottom surface of the proximal phalanx body 110 having the cylindrical shape (i.e., a portion of the proximal phalanx body 110 on which a bottom surface of the proximal phalanx portion of the user is located) is provided in a flat shape. Thus, the proximal phalanx portion of the user may be stably located in the proximal phalanx body 110. Moreover, one end portion of the proximal phalanx body 110 has a ' 7 ' shape and is joint-connected to a palm fixing part 150 to be described later. In other words, the one end portion of the proximal phalanx body 110 and the palm fixing part 150 are connected to each other by using a pin. At this time, a connection portion (i.e., a joint) of the proximal phalanx body 110 and the palm fixing part 150 may mean a first joint (MP Joint) of a finger.

A separate connection bracket 160 is provided between the proximal phalanx body 110 and the palm fixing part 150. In other words, the proximal phalanx body 110 is not connected directly to the palm fixing part 150 but is connected to the palm fixing part 150 through the connection bracket 160. The proximal phalanx body 110 is joint-connected to the connection bracket 160, and the palm fixing part 150 is also joint-connected to the connection bracket 160. Thus, the proximal phalanx body 110 can be rotated inward and outward with respect to the palm fixing part 150.

As described above, the robotic finger prosthesis 100 according to an embodiment of the inventive concepts further includes the palm fixing part 150. A palm of the user having only the remaining proximal phalanx portion of the finger is inserted into the palm fixing part 150. An inner circumferential surface of the palm fixing part 150 is a curved surface, and the portion of the palm fixing part 150 into which the palm is inserted has a U-shape. Thus, the palm of the user is stably inserted into and fixed in the palm fixing part 150. As described above, the palm fixing part 150 is connected to the proximal phalanx body 110 through the connection bracket 160. The palm fixing part 150 and the proximal phalanx body 110 are connected to each other via the connection bracket 160, and thus the palm fixing part 150 can be rotated in left and right directions with respect to the proximal phalanx body 110 or the first proximal phalanx link 112. As a result, the user may conveniently use the robotic finger prosthesis 100.

The middle phalanx body 120 is connected to the proximal phalanx body 110 to perform a function of the cut middle phalanx portion of the user. In detail, the middle phalanx body 120 may mean the middle phalanx of the finger, i.e., a second phalanx of the finger. The middle phalanx body 120 includes two members disposed in parallel to each other, and the two members are connected to each other through a separate member disposed therebetween. The middle phalanx body 120 is connected to both end portions of the proximal phalanx body 110, and the middle phalanx body 120 and the proximal phalanx body 110 are joint-connected to each other. In other words, the middle phalanx body 120 and the proximal phalanx body 110 are connected to each other by using a pin. A joint of the middle phalanx body 120 and the proximal phalanx body 110 means a second joint (PIP Joint) of the finger.

Meanwhile, an auxiliary bracket 140 is provided between the middle phalanx body 120 and the proximal phalanx body 110. In other words, the middle phalanx body 120 is not connected directly to the proximal phalanx body 110 but is connected to the proximal phalanx body 110 through the auxiliary bracket 140. The auxiliary bracket 140 has a triangular shape. In other words, the auxiliary bracket 140 includes two members which have triangular shapes and are disposed in parallel to each other, and the two members of the auxiliary bracket 140 are connected to each other through a separate member. A hole is formed in each of corners of the auxiliary bracket 140 having the triangular shape, and the middle phalanx body 120 and the proximal phalanx body 110 are joint-connected to the auxiliary bracket 140 through the holes of the auxiliary bracket 140. In an embodiment, first and third middle phalanx links 122 and 128 to be described later as well as the proximal phalanx body 110 and the middle phalanx body 120 may be joint-connected to the auxiliary bracket 140 through pins.

Referring to FIGS. 1 to 4, the distal phalanx body 130 is connected to the middle phalanx body 120 to perform a function of a cut distal phalanx portion of the finger. The distal phalanx body 130 means a distal phalanx of the finger, i.e., a last phalanx of the finger. In other words, the distal phalanx body 130 is a phalanx on which a nail is formed, i.e., a portion for performing a motion for grasping an object. The distal phalanx body 130 is connected to the middle phalanx body 120 and a second middle phalanx link 124 to be described later. The distal phalanx body 130 is joint-connected to the middle phalanx body 120 and the second middle phalanx link 124 by using pins. A joint of the distal phalanx body 130 and the middle phalanx body 120 means a third joint (DIP Joint) of the finger. An artificial nail having the same shape as a nail formed on a human finger is provided on a top end portion 131 of the distal phalanx body 130. A portion of the artificial nail provided on the top end portion 131 of the distal phalanx body 130 protrudes from the distal phalanx body 130. When an object is grasped using the robotic finger prosthesis 100 having the artificial nail, the object may be easily grasped by the artificial nail even though the object is thin. In addition, a pad 133 may be provided on a bottom end portion 132 of the distal phalanx body 130. The pad 133 formed on the bottom end portion 132 of the distal phalanx body 130 is substituted for a bottom surface of the finger. Thus, the pad 133 formed on the bottom end portion 132 of the distal phalanx body 130 may be formed of a soft material such as a silicon material. If the pad 133 is formed of a hard material or the same material as the distal phalanx body 130, it may be difficult to stably grasp an object, and a surface of an object may be damaged.

Referring to FIGS. 1 to 3, the first proximal phalanx link 112 is disposed under the proximal phalanx body 110. The first proximal phalanx link 112 is a member corresponding to a bottom of the finger of the user. The first proximal phalanx link 112 has a '⊏' shape of which one side is opened. One end portion of the first proximal phalanx link 112 formed in the shape having the opened one side is connected to the palm fixing part 150, and another end portion of the first proximal phalanx link 112 is connected to the second proximal phalanx link 114. The first proximal phalanx link 112 supports the proximal phalanx body 110. Meanwhile, the connection bracket 160 described above is provided between the first proximal phalanx link 112 and the palm fixing part 150. In other words, the first proximal phalanx link 112 is connected to the palm fixing part 150 through the connection bracket 160. Thus, the first proximal phalanx link 112 may be rotated in up and down directions with respect to the palm fixing part 150, and thus the user may conveniently use the robotic finger prosthesis 100.

Referring to FIGS. 1 to 4, the second proximal phalanx link 114 is disposed on the proximal phalanx body 110 and is joint-connected to the first proximal phalanx link 112. In more detail, the second proximal phalanx link 114 is located on one side portion of the proximal phalanx body 110, which is opposite to the palm fixing part 150 connected to the proximal phalanx body 110. The second proximal phalanx link 114 is joint-connected to both ends of the first proximal phalanx link 112 by using pins.

Here, in the motion of grasping an object using the robotic finger prosthesis 100 according to an embodiment of the inventive concepts, an angle between the first proximal phalanx link 112 and the second proximal phalanx link 114 increases since the first proximal phalanx link 112 comes in contact with the object and is pressed by the object. In addition, as the first proximal phalanx link 112 is pressed by the object while being in contact with the object, the second proximal phalanx link 114 applies force to the middle phalanx body 120, and thus the middle phalanx body 120 and the distal phalanx body 130 are folded inward. On the other hand, in the bending or stretching motion of the robotic finger prosthesis 100 in the state where an object is not in contact with the robotic finger prosthesis 100, the angle between the first proximal phalanx link 112 and the second proximal phalanx link 114 is fixed by the proximal phalanx elastic member 116. The proximal phalanx elastic member 116 is provided in the joint between the first proximal phalanx link 112 and the second proximal phalanx link 114 to provide elastic force.

In more detail, when the robotic finger prosthesis 100 performs the grasping motion for grasping an object, the angle between the first proximal phalanx link 112 and the second proximal phalanx link 114 is increased beyond an elastic force range of the proximal phalanx elastic member 116. In other words, the first proximal phalanx link 112 and the second proximal phalanx link 114 of the robotic finger prosthesis 100 may adapt to an envelope of an object to stably grasp the object. In addition, when the first proximal phalanx link 112 and the second proximal phalanx link 114 adapt to the envelope of the object, the first proximal phalanx link 112 is pressed by the object. Since the first proximal phalanx link 112 is pressed, the second proximal phalanx link 114 applies force to the middle phalanx body 120 to fold both the middle phalanx body 120 and the distal phalanx body 130 inward. As a result, when the robotic finger prosthesis 100 grasps an object, the middle phalanx body 120 and the distal phalanx body 130 as well as the first and second proximal phalanx links 112 and 114 adapt to the envelope of the object to stably grasp the object.

Meanwhile, the robotic finger prosthesis 100 may perform the bending or stretching motion in the state where it is not in contact with an object, as described above. When the robotic finger prosthesis 100 performs the bending or stretching motion, the angle between the first proximal phalanx link 112 and the second proximal phalanx link 114 is fixed. This is because the proximal phalanx elastic member 116 is disposed between the first proximal phalanx link 112 and the second proximal phalanx link 114. Thus, the angle between the first proximal phalanx link 112 and the second proximal phalanx link 114 is increased to an allowable limit of the elastic force range of the proximal phalanx elastic member 116. In other words, since the robotic finger prosthesis 100 can perform the bending or stretching motion even though it is not in contact with an object, external force is not applied to the first proximal phalanx link 112 and the second proximal phalanx link 114. In other words, since external force is not applied to the proximal phalanx elastic member 116, the angle between the first proximal phalanx link 112 and the second proximal phalanx link 114 is not increased but is fixed. In addition, the mechanical angle limiting element for limiting the angle between the first proximal phalanx link 112 and the second proximal phalanx link 114 is provided to at least one of the first proximal phalanx link 112 or the second proximal phalanx link 114. As illustrated in FIG. 1, the mechanical angle limiting element according to an embodiment of the inventive concepts is formed at each of joints of the first proximal phalanx link 112 and the second proximal phalanx link 114. Thus, in the bending or stretching motion of the robotic finger prosthesis 100, the angle between the first proximal phalanx link 112 and the second proximal phalanx link 114 is fixed at an angle of the mechanical angle limiting element by the proximal phalanx elastic member 116. In an embodiment, the proximal phalanx elastic member 116 is provided in pair at the joint between the first proximal phalanx link 112 and the second proximal phalanx link 114, i.e., at both ends of the joint of the first proximal phalanx link 112 and the second proximal phalanx link 114. The proximal phalanx elastic member 116 may be provided in the form of a torsion spring, not a general spring. Thus, the proximal phalanx elastic member 116 may increase or fix the angle between the first proximal phalanx link 112 and the second proximal phalanx link 114.

Referring to FIGS. 1 to 3, a first middle phalanx link 122 is disposed under the middle phalanx body 120, and one end portion of the first middle phalanx link 122 is joint-connected to the proximal phalanx body 110. In detail, the first middle phalanx link 122 is located between the two members of the middle phalanx body 120. The one end portion of the first middle phalanx link 122 is joint-connected to the auxiliary bracket 140, and another end portion of the first middle phalanx link 122 is joint-connected to a second middle phalanx link 124. The first middle phalanx link 122 is a member corresponding to a bottom of the finger of the user and assists a joint motion between the proximal phalanx body 110 and the distal phalanx body 130.

Referring to FIGS. 1 to 4, one end portion of the second middle phalanx link 124 is joint-connected to the other end portion of the first middle phalanx link 122, and another end portion of the second middle phalanx link 124 is joint-connected to the distal phalanx body 130. In detail, the one end portion of the second middle phalanx link 124 is joint-connected to the first middle phalanx link 122, and the other end portion of the second middle phalanx link 124 is joint-connected to the distal phalanx body 130.

Here, in the motion of grasping an object using the robotic finger prosthesis 100 according to an embodiment of the inventive concepts, an angle between the first middle phalanx link 122 and the second middle phalanx link 124 increases as the first middle phalanx link 122 comes in contact with the object and is pressed by the object. In addition, as the first middle phalanx link 122 is pressed by the object while being in contact with the object, the second middle phalanx link 124 applies force to the distal phalanx body 130, and thus the distal phalanx body 130 is folded inward. On the other hand, in the bending or stretching motion of the robotic finger prosthesis 100 in the state where an object is not in contact with the robotic finger prosthesis 100, the angle between the first middle phalanx link 122 and the second middle phalanx link 124 is fixed by a middle phalanx elastic member 126. The middle phalanx elastic member 126 is provided in the joint between the first middle phalanx link 122 and the second middle phalanx link 124 to provide elastic force.

In more detail, when the robotic finger prosthesis 100 performs the grasping motion for grasping an object, external force is applied to the first middle phalanx link 122 and the second middle phalanx link 123, and thus the angle between the first middle phalanx link 122 and the second middle phalanx link 124 is increased beyond an elastic force range of the middle phalanx elastic member 126. In other words, the first middle phalanx link 122 and the second middle phalanx link 124 of the robotic finger prosthesis 100 may adapt to an envelope of an object to stably grasp the object. In addition, when the first middle phalanx link 122 and the second middle phalanx link 124 adapt to the envelope of the object, the first middle phalanx link 122 is pressed by the object. As the first middle phalanx link 122 is pressed, the second middle phalanx link 124 applies force to the distal phalanx body 130, and thus the distal phalanx body 130 is folded inward. As a result, when the robotic finger prosthesis 100 grasps an object, the first middle phalanx link 122, the second middle phalanx link 124 and the distal phalanx body 130 adapt to the envelope of the object to stably grasp the object.

Meanwhile, the robotic finger prosthesis 100 may perform the bending or stretching motion in the state where it is not in contact with an object. When the robotic finger prosthesis 100 performs the bending or stretching motion, the angle between the first middle phalanx link 122 and the second middle phalanx link 124 is fixed. This is because the middle phalanx elastic member 126 is disposed between the first middle phalanx link 122 and the second middle phalanx link 124. Thus, the angle between the first middle phalanx link 122 and the second middle phalanx link 124 is increased to an allowable limit of the elastic force range of the middle phalanx elastic member 126. In other words, since the robotic finger prosthesis 100 can perform the bending or stretching motion even though it is not in contact with an object, external force is not applied to the first middle phalanx link 122 and the second middle phalanx link 124. In other words, since external force is not applied to the middle phalanx elastic member 126, the angle between the first middle phalanx link 122 and the second middle phalanx link 124 is not increased but is fixed. In addition, the mechanical angle limiting element for limiting the angle between the first middle phalanx link 122 and the second middle phalanx link 124 is provided to at least one of the first middle phalanx link 122 or the second middle phalanx link 124. As illustrated in FIGS. 1 and 4, the mechanical angle limiting element according to an embodiment of the inventive concepts is formed at each of joints of the first middle phalanx link 122 and the second middle phalanx link 124. Thus, in the bending or stretching motion of the robotic finger prosthesis 100, the angle between the first middle phalanx link 122 and the second middle phalanx link 124 is fixed at an angle of the mechanical angle limiting element by the middle phalanx elastic member 126. In an embodiment, the middle phalanx elastic member 126 may be provided in the form of a torsion spring, like the proximal phalanx elastic member 116. Thus, the angle between the first middle phalanx link 122 and the second middle phalanx link 124 may be increased or fixed.

Referring to FIGS. 1, 2 and 4, a third middle phalanx link 128 is disposed on the middle phalanx body 120 and connects the proximal phalanx body 110 and the distal phalanx body 130 to each other. In more detail, the third middle phalanx link 128 is disposed on the middle phalanx body 120 to connect the proximal phalanx body 110 to the distal phalanx body 130. Here, one end portion of the third middle phalanx link 128 is joint-connected to the auxiliary bracket 140, and another end portion of the third middle phalanx link 128 is joint-connected to the distal phalanx body 130. The third middle phalanx link 128 assists movement of the second joint (PIP Joint) and the third joint (DIP Joint) of the finger.

The robotic finger prosthesis 100 including the aforementioned components according to the embodiment of the inventive concepts may perform the bending or stretching motion by using only the proximal phalanx portion of the user having the cut finger. In addition, since the robotic finger prosthesis 100 adapts to various-shaped objects M, a contact area between the robotic finger prosthesis 100 and the object M may be increased to stably perform the grasping motion.

Motion states of the robotic finger prosthesis 100 according to an embodiment of the inventive concepts will be described hereinafter with reference to FIGS. 5 to 8.

FIG. 5 is a schematic view illustrating mechanism of bending and stretching motions of the adaptive robotic finger prosthesis of FIG. 1, and FIG. 6 is a schematic view illustrating the bending and stretching motions according to the motion mechanism of the adaptive robotic finger prosthesis illustrated in FIG. 5. FIGS. 7A-7D illustrate mechanism of a grasping motion of the adaptive robotic finger prosthesis of FIG. 1, and FIG. 8 is a schematic view illustrating the grasping motion according to the motion mechanism of the adaptive robotic finger prosthesis illustrated in FIGS. 7A-7D.

As illustrated in FIGS. 5 to 8, the robotic finger prosthesis 100 according to an embodiment of the inventive concepts may mainly perform two motions of a finger, i.e., the bending or stretching motion of the finger and the motion for grasping an object. As described above, the robotic finger prosthesis 100 is worn or mounted on the proximal phalanx portion of the cut finger and uses power (or force) of the proximal phalanx portion. The robotic finger prosthesis 100 is based on the 5-bar link. However, the motion of the link involved in the bending or stretching motion performed in the state where the robotic finger prosthesis 100 is not in contact with the object M is different from the motion of the link involved in the grasping motion of the object M performed in the state where the robotic finger prosthesis 100 is in contact with the object M.

In this regard, mechanism of the robotic finger prosthesis 100 will be described with reference to FIG. 5, and the bending or stretching motion of the robotic finger prosthesis 100 will be described with reference to FIG. 6.

Referring to FIG. 5, the robotic finger prosthesis 100 is based on a motion of the 5-bar link. The proximal phalanx body 110, the middle phalanx body 120, the distal phalanx body 130, the first proximal phalanx link 112, the second proximal phalanx link 114, the first middle phalanx link 122 and the second middle phalanx 124 are involved in the 5-bar link motion.

The first proximal phalanx link 112 and the first middle phalanx link 122 are members corresponding to bottoms of the finger and are links which come in direct contact with the object M. Here, the second proximal phalanx link 114 and the proximal phalanx elastic member 116 are provided at the joint portion of the first proximal phalanx link 112, and the second middle phalanx link 124 and the middle phalanx elastic member 126 are provided at the joint portion of the first middle phalanx link 122. The first joint (MP Joint) of the finger is a fixed portion and corresponds to the joint (or a connection portion) between the palm fixing part 150 and the proximal phalanx body 110. In addition, the second joint (PIP Joint) of the finger corresponds to the joint between the proximal phalanx body 110 and the middle phalanx body 120, and the third joint (DIP Joint) of the finger correspond to the joint between the middle phalanx body 120 and the distal phalanx body 130.

As illustrated in FIGS. 5 and 6, in the simple bending or stretching motion in the state where the robotic finger prosthesis 100 is not in contact with the object M, the first proximal phalanx link 112 and the first middle phalanx link 122 are fixed by the second proximal phalanx link 114, the proximal phalanx elastic member 116, the second middle phalanx link 124 and the middle phalanx elastic member 126, which are provided at the joints of the first proximal phalanx link 112 and the first middle phalanx link 122. At this time, virtual links are formed between the palm fixing part 150 and the proximal phalanx body 110 and between the proximal phalanx body 110 and the middle phalanx body 120. Since the first proximal phalanx link 112 and the first middle phalanx link 122 are fixed, the virtual links have fixed constant values. Thus, the robotic finger prosthesis 100 realizes a 4-bar link motion to perform the bending or stretching motion. Here, the fact that the first proximal phalanx link 112 is fixed means that the angle between the first and second proximal phalanx links 112 and 114 is limited to the angle of the mechanical angle limiting element by the proximal phalanx elastic member 116, and the fact that the first middle phalanx link 122 is fixed means that the angle between the first and second middle phalanx links 122 and 124 is limited to the angle of the mechanical angle limiting element by the middle phalanx elastic member 126. Thus, when the robotic finger prosthesis 100 performs the bending or stretching motion, the joint (i.e., the second joint (PIP Joint)) of the proximal phalanx body 110 and the middle phalanx body 120 is folded by the proximal phalanx elastic member 116 and the mechanical angle limiting element which are provided between the first proximal phalanx link 112 and the second proximal phalanx link 114. In addition, the joint (i.e., the third joint (DIP Joint)) of the middle phalanx body 120 and the distal phalanx body 130 is folded by the middle phalanx elastic member 126 and the mechanical angle limiting element which are provided between the first middle phalanx link 122 and the second middle phalanx link 124. Thus, the robotic finger prosthesis 100 may perform the bending motion like an actual finger.

The grasping motion of the robotic finger prosthesis 100 according to an embodiment of the inventive concepts will be described with reference to FIGS. 5, 7 and 8.

When external force is applied to the first proximal phalanx link 112 and the first middle phalanx link 122, an angle between the first proximal phalanx link 112 and the first middle phalanx link 122 is increased, and a virtual link is formed at this time. In other words, when the angle between the first proximal phalanx link 112 and the first middle phalanx link 122 is increased, the formed virtual link is lengthened, and thus the second joint (PIP Joint) and the third joint (DIP Joint) of the finger are rotated to adapt to an envelope of the object M. Here, a fact that the angle of the first proximal phalanx link 112 is increased means that the external force is applied to the proximal phalanx elastic member 116 provided between the first and second proximal phalanx links 112 and 114 to increase the angle between the first and second proximal phalanx links 112 and 114, and a fact that the angle of the first middle phalanx link 122 is increased means that the external force is applied to the middle phalanx elastic member 126 provided between the first and second middle phalanx links 122 and 124 to increase the angle between the first and second middle phalanx links 122 and 124.

Referring to first and second views of FIG. 8, the robotic finger prosthesis 100 performs the 4-bar link motion until it comes in contact with the object M. When the robotic finger prosthesis 100 performs the motion for grasping the object M, the first proximal phalanx link 112 and the first middle phalanx link 122 come in contact with the object M and are pressed by the object M, as illustrated in third and fourth views of FIG. 8. In this case, the external force is applied to the first proximal phalanx link 112 and the first middle phalanx link 122, and thus the angle between the first and second proximal phalanx links 112 and 114 is increased and the angle between the first and second middle phalanx links 122 and 124 is increased. When the first proximal phalanx link 112 and the first middle phalanx link 122 are pressed, the second proximal phalanx link 114 applies force to the middle phalanx body 120, and thus the middle phalanx body 120 is folded inward. Continuously, the middle phalanx body 120 comes in contact with the object M, and thus the second middle phalanx link 124 applies force to the distal phalanx body 130. As a result, the distal phalanx body 130 is folded inward. At this time, the folding motion of the distal phalanx body 130 is easily performed by the third middle phalanx link 128 connected to the second middle phalanx link 124. Accordingly, an area of a contact portion of the robotic finger prosthesis 100 is increased to meet an outward shape of the object M. As a result, the robotic finger prosthesis 100 may stably grasp the object M.

The robotic finger prosthesis according to an embodiment of the inventive concepts is described above with reference to FIGS. 1 to 8. Hereinafter, a robotic driving mechanism and a method of driving the same according to other embodiments of the inventive concepts will be described with reference to FIGS. 9 to 22.

FIG. 9 is a schematic view illustrating a link of a robotic driving mechanism according to a first embodiment of the inventive concepts, FIGS. 10A and 10B illustrate a cross-sectional view and a perspective view of the robotic driving mechanism according to the first embodiment of the inventive concepts, and FIG. 11 is an exploded perspective view illustrating the robotic driving mechanism according to the first embodiment of the inventive concepts.

Referring to FIGS. 9 to 11, a robotic driving mechanism 1000 according to a first embodiment of the inventive concepts may include a first link part 1100, a second link part 1200, and a third link part 1300. The first link part 1100, the second link part 1200 and the third link part 1300 may be stacked and may receive driving force at a node A through an actuator MA to perform bending, stretching and grasping motions. Hereinafter, each of the components will be described in detail.

First Link Part 1100

The first link part 1100 may include a first input link 1110 which receives driving force F through an actuator MA and of which a length is controlled according to a motion of grasping an object. At this time, one end of the first link part 1100 may be connected to the actuator MA through a connector C.

The first input link 1110 may receive the driving force F from the actuator MA through the node A. The first input link 1110 may be moved in an X-axis direction by the driving force F received from the actuator MA, thereby transferring the driving force F received from the node A to a node C1. Thus, a grasping link to be described later may be rotated to grasp an object.

The length of the first input link 1110 may be variable. To achieve this, the first input link 1110 may include a first elastic part 1112 provided at one side of the first input link 1110. When the actuator MA pushes the node A, the first elastic part 1112 may be contracted, and thus the length of the first input link 1110 may be shortened. When the driving force F from the actuator MA is removed after the first elastic part 1112 is contracted, the first elastic part 1112 may be restored, and thus the length of the first input link 1110 may be lengthened. As a result, the length of the first input link 1110 may be controlled by the contraction and restoration of the first elastic part 1112. The first elastic part 1112 will be described later in more detail.

The first link part 1110 may include a first side link 1132, a first top link 1134, and a first grasping link 1142. In other words, the first side link 1132, the first top link 1134 and the first grasping link 1142 may constitute a 3-bar link having a triangle shape and may be defined as a first output link.

The first side link 1132 may mean a link connecting a node B and a node C1'. The first side link 1132 may receive the driving force F from the actuator MA through the node C1. In other words, when the first input link 1110 pushes the node C1 in the X-axis direction, the first side link 1132 may be rotated in a clockwise direction to transfer the driving force F to the first top link 1134.

The first top link 1134 may mean a link connecting the node C1' and a node D. The first top link 1134 may receive the driving force F from the first side link 1132 and may transfer the received driving force F to the first grasping link 1142.

The first grasping link 1142 may mean a link connecting the node B and the node D. In other words, both nodes of the first grasping link 1142 may be shared with the first side link 1132 and the first top link 1134, respectively. The first grasping link 1142 may be rotated ($\theta 1$) about the node B in a clockwise direction by the driving force F transferred from the first top link 1134. Thus, the first grasping link 1142 may be rotated to grasp an object located under the first grasping link 1142. When the driving force F is removed, the first grasping link 1142 may be restored in a counterclockwise direction.

Second Link Part 1200

The second link part 1200 may include a second input link 1210 which receives driving force F through an actuator MA and of which a length is controlled according to a motion of grasping an object. One end of the second link part 1200 may also be connected to the actuator MA through the connector C.

The second input link 1210 may receive the driving force F from the actuator MA through the node A. The second input link 1210 may be moved in the X-axis direction by the driving force F received from the actuator MA, thereby transferring the driving force F received from the node A to a node C2. Thus, a grasping link to be described later may be rotated to grasp an object.

The length of the second input link 1210 may be variable. To achieve this, the second input link 1210 may include a second elastic part 1212 provided at one side of the second input link 1210. When the actuator MA pushes the node A, the second elastic part 1212 may be contracted, and thus the length of the second input link 1210 may be shortened. When the driving force F from the actuator MA is removed after the second elastic part 1212 is contracted, the second elastic part 1212 may be restored, and thus the length of the second input link 1210 may be lengthened. As a result, the length of the second input link 1210 may be controlled by the contraction and restoration of the second elastic part 1212. Here, the second elastic part 1212 of the second input link 1210 may be longer than the first elastic part 1112 of the first input link 1110. The second elastic part 1212 will be described later in more detail.

According to an embodiment, the second input link 1210 may receive the driving force F from the actuator MA which is the same as the actuator MA providing the driving force F to the first input link 1110. In other words, the first and second input links 1110 and 1210 may receive the driving force F from a single actuator MA at the same time.

The second link part 1200 may include a second transfer link part and a second output link part.

The second transfer link part may include a (2-1)th side link 1232, a (2-1)th top link 1234, a (2-2)th side link 1236, a (2-2)th top link 1238, a (2-3)th side link 1240, and a second bottom link 1242.

The (2-1)th side link 1232 may mean a link connecting a node B and a node C2', and the (2-1)th top link 1234 may mean a link connecting the node C2' and a node E2. The (2-2)th side link 1236 may mean a link connecting a node E2' and a node D', and the (2-2)th top link 1238 may mean a link connecting the node E2' and a node F2. The (2-3)th side link 1240 may mean a link connecting the node F2 and a node D, and the second bottom link 1242 may mean a link connecting the node B and the node D.

Thus, the (2-1)th side link 1232, the (2-1)th top link 1234, the (2-2)th side link 1236, the (2-2)th top link 1238, the (2-3)th side link 1240 and the second bottom link 1242 may constitute a 2-stage 4-bar link.

The driving force F provided from the actuator MA may be transferred to the node C2 of the (2-1)th side link 1232 through the second input link 1210. When the driving force F is provided to the (2-1)th side link 1232, the driving force F may be transferred to the second bottom link 1242 through the (2-1)th top link 1234, the (2-2)th side link 1236, the (2-2)th top link 1238, and the (2-3)th side link 1240. Thus, the second bottom link 1242 may be rotated ($\theta 1$) in a clockwise direction. Thus, the second bottom link 1242 may be rotated to grasp an object located under the second bottom link 1242. When the driving force F is removed, the second bottom link 1242 may be restored in a counterclockwise direction.

The second link part 1200 may also include the second output link part provided at a side in a +X-axis direction of the second transfer link part.

The second output link part may include a (2-3)th top link 1244 and a second grasping link 1246.

The (2-3)th top link 1244 may mean a link connecting the node F2 and a node G. The (2-3)th top link 1244 may receive the driving force F from the (2-3)th side link 1240 and may transfer the received driving force F to the second grasping link 1246.

The second grasping link 1246 may mean a link connecting the node D and the node G. In other words, both nodes of the second grasping link 1246 may be shared with the (2-3)th side link 1240 and the (2-3)th top link 1244, respectively. The second grasping link 1246 may be rotated ($\theta 2$)

about the node D in a clockwise direction by the driving force F transferred from the second transfer link part, i.e., the (2-3)th side link 1240. Thus, the second grasping link 1246 may be rotated to grasp an object located under the second grasping link 1246. When the driving force F is removed, the second grasping link 1246 may be restored in a counterclockwise direction.

According to an embodiment, the first grasping link 1142 and the second bottom link 1242 may be rotated together about the node B by the same angle θ1 to grasp an object, and the second grasping link 1246 may be rotated about the node D by the angle θ2 to grasp the object. Here, the rotation angles θ1 and θ2 with respect to the X-axis may satisfy a condition of θ2≥θ1. As a result, the first and second link parts 1100 and 1200 may perform a motion similar to a motion of a finger.

Third Link Part 1300

The third link part 1300 may include a third input link 1310 which receives driving force F through an actuator MA and which has a constant length. One end of the third link part 1300 may also be connected to the actuator MA through the connector C. In other words, the driving force F provided from the actuator MA may be transferred to the first to third link parts 1100, 1200 and 1300 through the connector C at the same time (see FIG. 10B).

The third input link 1310 may receive the driving force F from the actuator MA through the node A. The third input link 1310 may be moved in the X-axis direction by the driving force F received from the actuator MA, thereby transferring the driving force F received from the node A to a node C3. Thus, a grasping link to be described later may be rotated to grasp an object.

The length of the third input link 1310 may be constant. In other words, the third input link 1310 may have the constant length, unlike the first and second input links 1110 and 1210. Since the length of the third input link 1310 is constant, the grasping link of the third link part 1300 may grasp an object with a stronger force.

According to an embodiment, the third input link 1310 may receive the driving force F from the actuator MA which is the same as the actuator MA providing the driving force F to the first input link 1110 and the second input link 1210. In other words, the first to third input links 1110, 1210 and 1310 may receive the driving force F from a single actuator MA at the same time.

The third link part 1300 may include a third transfer link part and a third output link part.

The third transfer link part may include a third front transfer link part and a third back transfer link part.

The third front transfer link part may include a (3-1)th side link 1332, a (3-1)th top link 1334, a (3-2)th side link 1336, a (3-2)th top link 1338, a (3-3)th side link 1340, and a (3-1)th bottom link 1342.

The (3-1)th side link 1332 may mean a link connecting a node B and a node C3', and the (3-1)th top link 1334 may mean a link connecting the node C3' and a node E3. The (3-2)th side link 1336 may mean a link connecting a node E3' and a node D', and the (3-2)th top link 1338 may mean a link connecting the node E3' and a node F3. The (3-3)th side link 1340 may mean a link connecting a node F3' and a node D, and the (3-1)th bottom link 1242 may mean a link connecting the node B and the node D.

Thus, the (3-1)th side link 1332, the (3-1)th top link 1334, the (3-2)th side link 1336, the (3-2)th top link 1338, the (3-3)th side link 1340 and the (3-1)th bottom link 1342 may constitute a 2-stage 4-bar link.

When the driving force F is provided from the actuator MA to the node C3 of the (3-1)th side link 1332 through the third input link 1310, the driving force F may be transferred to the (3-1)th bottom link 1342 through the (3-1)th top link 1334, the (3-2)th side link 1336, the (3-2)th top link 1338, and the (3-3)th side link 1340. Thus, the (3-1)th bottom link 1342 may be rotated (θ1) in a clockwise direction. Thus, the (3-1)th bottom link 1342 may be rotated to grasp an object located under the (3-1)th bottom link 1342. When the driving force F is removed, the (3-1)th bottom link 1342 may be restored in a counterclockwise direction.

The third link part 1300 may also include the third back transfer link part provided at a side in a +X-axis direction of the third front transfer link part.

The third back transfer link part may include the (3-3)th side link 1340, a (3-3)th top link 1344, a (3-4)th side link 1345, and a (3-2)th bottom link 1346.

The (3-3)th side link 1340 may be the link connecting the node D and the node F3', as described above. The (3-3)th top link 1344 may mean a link connecting the node F3' and a node H3, the (3-4)th side link 1345 may mean a link connecting the node H3 and a node G, and the (3-2)th bottom link 1346 may mean a link connecting the node D and the node G.

Thus, the (3-3)th side link 1340, the (3-3)th top link 1344, the (3-4)th side link 1345 and the (3-2)th bottom link 1346 may constitute a 1-stage 4-bar link.

The driving force F of the actuator MA may be transferred to the (3-3)th side link 1340 through the (3-1)th side link 1332, the (3-1)th top link 1334, the (3-2)th side link 1336, and the (3-2)th top link 1338. The driving force F transferred to the (3-3)th side link 1340 may be transferred to the (3-2)th bottom link 1346 through the (3-3)th top link 1344 and the (3-4)th side link 1345. Thus, the (3-2)th bottom link 1346 may be rotated (θ2) in a clockwise direction. As a result, the (3-2)th bottom link 1346 may grasp an object located under the (3-2)th bottom link 1346. When the driving force F is removed, the (3-2)th bottom link 1346 may be restored in a counterclockwise direction.

The third link part 1300 may also include the third output link part provided at a side in a +X-axis direction of the third back transfer link part.

The third output link part may include a (3-4)th top link 1348 and a third grasping link 1350.

The (3-4)th top link 1348 may mean a link connecting the node H3 and a node I. The (3-4)th top link 1348 may receive the driving force F from the (3-4)th side link 1345 and may transfer the received driving force F to the third grasping link 1350.

The third grasping link 1350 may mean a link connecting the node G and the node I. In other words, both nodes of the third grasping link 1350 may be shared with the (3-4)th side link 1345 and the (3-4)th top link 1348, respectively. The third grasping link 1350 may be rotated (θ3) about the node G in a clockwise direction by the driving force F transferred from the third transfer link part, i.e., the (3-4)th side link 1345. Thus, the third grasping link 1350 may be rotated to grasp an object located under the third grasping link 1350. When the driving force F is removed, the third grasping link 1350 may be restored in a counterclockwise direction.

According to an embodiment, the first grasping link 1142, the second bottom link 1242 and the (3-1)th bottom link 1342 may be rotated together about the node B by the same angle θ1 to grasp an object. In addition, the second grasping link 1246 and the (3-2)th bottom link 1346 may be rotated together about the node D by the same angle θ2 to grasp the object. Furthermore, the third grasping link 1350 may be rotated about the node G by the angle θ3 to grasp the object. Here, the rotation angles θ1, θ2 and θ3 with respect to the X-axis may satisfy a condition of θ3≥θ2≥θ1. As a result, the first to third link parts 1100, 1200 and 1300 may perform a motion similar to a motion of a finger.

The first to third link parts 1100, 1200 and 1300 according to an embodiment of the inventive concepts were described above. The first to third link parts 1100, 1200 and 1300 according to an embodiment of the inventive concepts may be stacked.

The first input link 1110 of the first link part 1100, the second input link 1210 of the second link part 1200 and the third input link 1310 of the third link part 1300 may be stacked on each other. At this time, the node A of the first input link 1110, the node A of the second input link 1210 and the node A of the third input link 1310 may be shared with each other. Here, the fact that the nodes are shared with each other may mean that the nodes are co-axial. Since the nodes A are shared with each other, the driving force F of the actuator MA may be provided to the first to third input links 1110, 1210 and 1310 at the same time.

The first output link of the first link part 1100, the second transfer link part of the second link part 1200 and the third front transfer link part of the third link part 1300 may overlap with each other and may be stacked on each other.

At least one of the nodes of the first grasping link 1142 of the first link part 1100 may be shared with the second transfer link part of the second link part 1200 and the third front transfer link part of the third link part 1300. For example, the node B of the first grasping link 1142 of the first link part 1100, the node B of the second bottom link 1242 of the second link part 1200 and the node B of the (3-1)th bottom link 1342 of the third link part 1300 may be shared with each other. In another aspect, the node B may be shared with one end node of a base 1020 on which the actuator MA is provided (see FIG. 10A).

In addition, the node D of the first grasping link 1142 of the first link part 1100, the node D of the second bottom link 1242 of the second link part 1200 and the node D of the (3-1)th bottom link 1342 of the third link part 1300 may be shared with each other. To achieve this, the first grasping link 1142, the second bottom link 1242 and the (3-1)th bottom link 1342 may have the same length L1. Since the nodes B and the nodes D of the first to third link parts 1100, 1200 and 1300 are shared, the first grasping link 1142, the second bottom link 1242 and the (3-1)th bottom link 1342 may be rotated (θ1) together in the clockwise direction.

The second output link part of the second link part 1200 and the third back transfer link part of the third link part 1300 may overlap with each other and may be stacked on each other. At least one of the nodes of the second grasping link 1246 of the second link part 1200 may be shared with the third back transfer link part of the third link part 1300. For example, the node D of the second grasping link 1246 of the second link part 1200 may be shared with the node D of the (3-2)th bottom link 1346 (i.e., the (3-1)th bottom link 1342) of the third link part 1300, and the node G of the second grasping link 1246 of the second link part 1200 may be shared with the node G of the (3-2)th bottom link 1346 (i.e., the third grasping link 1350) of the third link part 1300. To achieve this, the second grasping link 1246 and the (3-2)th bottom link 1346 may have the same length L2. Since the nodes D and the nodes G of the second grasping link 1246 and the (3-2)th bottom link 1346 are shared, the second grasping link 1246 and the (3-2)th bottom link 1346 may be rotated (θ2) together in the clockwise direction.

The link of the robotic driving mechanism according to the first embodiment of the inventive concepts was described above with reference to FIGS. 9 to 11. Hereinafter, experimental results of bending and stretching motions of the robotic driving mechanism according to the first embodiment of the inventive concepts will be described with reference to FIGS. 12 and 13.

FIGS. 12 and 13 show experimental results of bending and stretching motions of the robotic driving mechanism according to the first embodiment of the inventive concepts.

Referring to FIG. 12, the first grasping link 1142, the second grasping link 1246 and the third grasping link 1350 of the robotic driving mechanism 1000 according to the first embodiment may be parallel to the X-axis in an initial state. When the driving force F (e.g., external force) is applied from the actuator MA to the node A, each of the link parts may be rotated in the clockwise direction. For example, the first grasping link 1142, the second grasping link 1246 and the third grasping link 1350 may be rotated in the clockwise direction. Here, when the actuator MA moves in the X-axis direction by a predetermined distance, the first grasping link 1142 may be rotated by −90 degrees (θ1 of FIG. 9), the second grasping link 1246 may be rotated by −180 degrees (θ2 of FIG. 9), and the third grasping link 1350 may be rotated by −270 degrees (θ3 of FIG. 9).

As illustrated in FIG. 13, when the actuator MA moves in the +X-axis direction by 20 mm, the first grasping link 1142 may be rotated by −90 degrees, the second grasping link 1246 may be rotated by −180 degrees, and the third grasping link 1350 may be rotated by −270 degrees. On the contrary, when the actuator MA moves from a position of +20 mm to a position of 0 mm in a −X-axis direction, the first grasping link 1142, the second grasping link 1246 and the third grasping link 1350 may be restored to the initial state of 0 degree.

Thus, the bending and stretching motions of the robotic driving mechanism according to the first embodiment of the inventive concepts may be performed.

Hereinafter, a grasping motion of the robotic driving mechanism according to the first embodiment of the inventive concepts will be described with reference to FIGS. 14 to 16.

FIGS. 14 to 16 are schematic views illustrating a grasping motion of the robotic driving mechanism according to the first embodiment of the inventive concepts. In more detail, FIGS. 14 to 16 mainly illustrates the node B of FIG. 9 in detail. For the purpose of ease and convenience in explanation, some links between the side link and the grasping link are omitted. The grasping motion according to an embodiment of the inventive concepts will be described with reference to FIGS. 9 to 11 and 14 to 16 for the purpose of ease and convenience in explanation.

The robotic driving mechanism according to the first embodiment of the inventive concepts may actively adapt to an outward shape of an object to accurately grasp the object.

For example, when the driving force F is continuously provided to the first input link 1110 through the actuator MA in a state where the first grasping link 1142 of the first link part 1100 grasps an object, the first elastic part 1112 is contracted, and thus the length of the first input link 1110 is shortened. In other words, a distance from the node A to the node B in the X-axis direction is reduced from a distance Do to a distance D1. At this time, the second grasping link 1246 of the second link part 1200 may be rotated to grasp the object even though the length of the first input link 1110 is shortened.

In addition, when the driving force F is continuously provided to the second input link 1210 through the actuator MA in a state where the second grasping link 1246 of the second link part 1200 grasps the object, the second elastic part 1212 is contracted, and thus the length of the second input link 1210 is shortened. At this time, the third grasping link 1350 of the third link part 1300 may be rotated to grasp the object even though the lengths of the first and second input links 1110 and 1210 are shortened.

Referring to FIG. 14 for more detailed descriptions, the initial state in which external force does not exist (see a dotted line) may be changed into a state in which external force (i.e., the driving force F) is applied (see a full line). In detail, when the driving force F is applied to the node A by the actuator MA, the node A is moved from a position O in the X-axis direction. In other words, the nodes A of the first to third input links 1110, 1210 and 1310 are moved in the X-axis direction. Thus, the node C1 of the first input link 1110, the node C2 of the second input link 1210 and the node C3 of the third input link 1310 push the first side link 1132, the (2-1)th side link 1232 and the (3-1)th side link 1332, respectively. Thus, the first side link 1132, the (2-1)th side link 1232 and the (3-1)th side link 1332 are rotated in a direction R. As the first side link 1132 is rotated, the driving force is transferred through middle links (not shown) to rotate the first grasping link 1142 from the initial state (an angle of 0 degree with respect to the X-axis) by the angle θ1. In addition, as the (2-1)th side link 1232 is rotated, the second bottom link 1242 is rotated from the initial state by the angle θ1. Furthermore, as the (3-1)th side link 1332 is rotated, the (3-1)th bottom link 1342 is rotated from the initial state by the angle θ1.

Since the driving force is applied, the first grasping link 1142, the second bottom link 1242 and the (3-1)th bottom link 1342 of which motions are dependent on each other by the shared node may be continuously rotated to come in contact with the object. Thus, the distance between the node A and the node B may be reduced from the distance D1 to a distance D2. When the object is grasped by (i.e., comes in contact with) the first grasping link 1142, the second bottom link 1242 and the (3-1)th bottom link 1342, the rotation of the first grasping link 1142, the second bottom link 1242 and the (3-1)th bottom link 1342 may be stopped. The present step will be described in more detail with reference to FIG. 15.

Referring to FIG. 15, the rotation of the first grasping link 1142, the second bottom link 1242 and the (3-1)th bottom link 1342 may be stopped even though the actuator MA continuously moves in the +X-axis direction in the state where the object is grasped by the first grasping link 1142, the second bottom link 1242 and the (3-1)th bottom link 1342. In other words, the first grasping link 1142, the second bottom link 1242 and the (3-1)th bottom link 1342 may be maintained in the state where they grasp the object.

When the driving force F is continuously provided through the actuator MA in the state where the first grasping link 1142, the second bottom link 1242 and the (3-1)th bottom link 1342 grasp the object, the length of the first input link 1110 may be shortened. In other words, a length of the first elastic part 1112 of the first input link 1110 may be shortened. Since the length of the first input link 1110 is shortened, the second input link 1210 and the third input link 1310 may have additional degrees of freedom. Thus, the second input link 1210 may additionally push the node C2, and the third input link 1310 may additionally push the node C3. Accordingly, rotational displacement may not occur at the first side link 1132 since the object is grasped by the first grasping link 1142, but the (2-1)th side link 1232 and the (3-1)th side link 1332 may be additionally rotated in the clockwise direction R.

As the (2-1)th side link 1232 and the (3-1)th side link 1332 are additionally rotated, the second grasping link 1246 and the (3-2)th bottom link 1346 may be rotated (θ2) in the clockwise direction. In other words, even though the first grasping link 1142, the second bottom link 1242 and the (3-1)th bottom link 1342 grasp the object and the rotational displacement no longer occurs, the second grasping link 1246 and the (3-2)th bottom link 1346 are additionally rotated to grasp the object. Thereafter, when the actuator MA continuously moves in the +X-axis direction, the distance between the node A and the node B may be reduced from the distance D2 to a distance D3, and the rotation of the second grasping link 1246 and the (3-2)th bottom link 1346 may be stopped since they 1246 and 1346 are in contact with the object. The present step will be described in more detail with reference to FIG. 16.

Referring to FIG. 16, the rotation of the second grasping link 1246 and the (3-2)th bottom link 1346 may be stopped even though the actuator MA continuously moves in the +X-axis direction in the state where the object is grasped by the second grasping link 1246 and the (3-2)th bottom link 1346. In other words, the second grasping link 1246 and the (3-2)th bottom link 1346 may be maintained in the state where they grasp the object.

When the driving force F is continuously provided through the actuator MA in the state where the second grasping link 1246 and the (3-2)th bottom link 1346 grasp the object, the lengths of the first and second input links 1110 and 1210 may be shortened. In other words, the length of the first elastic part 1112 of the first input link 1110 may be shortened, and a length of the second elastic part 1212 of the second input link 1210 may be shortened. Since the lengths of the first and second input links 1110 and 1210 are shortened, the third input link 1310 may have an additional degree of freedom. Thus, the third input link 1310 may additionally push the node C3. Accordingly, rotational displacement may not occur at the (2-1)th side link 1232 since the object is grasped by the second grasping link 1246, but the (3-1)th side link 1332 may be additionally rotated in the clockwise direction R.

As the (3-1)th side link 1332 is additionally rotated by the driving force F, the third grasping link 1350 may be rotated (θ3) in the clockwise direction. In other words, even though the first and second link parts 1100 and 1200 grasp the object and the rotational displacement no longer occurs at the first and second link parts 1100 and 1200, the third grasping link 1350 may be additionally rotated to grasp the object.

According to the first embodiment of the inventive concepts described above, each of the first to third link parts 1100, 1200 and 1300 comes in contact with the object to grasp the object. This is because when the first grasping link 1142, the second bottom link 1242 and the (3-1)th bottom link 1342 are in contact with the object, the length of the first input link 1110 is reduced to provide the additional degree of freedom such that the second grasping link 1246 and the (3-2) bottom link 1346 come in contact with the object. In addition, this is because when the second grasping link 1246 and the (3-2)th bottom link 1346 are in contact with the object, the length of the second input link 1210 is reduced to provide the additional degree of freedom such that the third grasping link 1350 comes in contact with the object.

The grasping motion of the robotic driving mechanism according to the first embodiment was described above. Hereinafter, experimental results of the grasping motion of the robotic driving mechanism according to the first embodiment of the inventive concepts will be described with reference to FIGS. 17 to 19.

FIGS. 17 to 19 show experimental results of the grasping motion of the robotic driving mechanism according to the first embodiment of the inventive concepts.

Referring to FIG. 17, to grasp an object Obj, the driving force F may be provided from the actuator MA in the +X-axis direction. Thus, the first to third link parts 1100, 1200 and 1300 may be rotated in the clockwise direction. Thus, the first grasping link 1142 of the first link part 1100, the second bottom link 1242 of the second link part 1200 and the (3-1)th bottom link 1342 of the third link part 1300 may come in contact with a first contact point CT1 of the object Obj. The second bottom link 1242 and the (3-1)th bottom link 1342 are rotated together with the first grasping link 1142. As illustrated in FIG. 18, first contact may occur when the actuator MA moves by about 9 mm in the +X-axis direction, i.e., at the first contact point CT1 located at about −50 degrees.

Thereafter, when the actuator MA continuously moves in the +X-axis direction, the first elastic part 1112 of the first input link 1110 may be contracted. As illustrated in FIG. 19, when the actuator MA moves in the +X-axis direction after the first contact, the length of the first input link 1110 may be reduced from about 43.5 mm.

In addition, when the actuator MA continuously moves in the +X-axis direction, the length of the first input link 1110 may be contracted to rotate the second grasping link 1246 and the (3-2)th bottom link 1346 in the clockwise direction. Thus, the second grasping link 1246 and the (3-2)th bottom link 1346 may come in contact with a second contact point CT2 of the object Obj. As illustrated in FIG. 18, second contact may occur when the actuator MA moves by about 10.5 mm in the +X-axis direction, i.e., at the second contact point CT2 located at about −90 degrees.

Thereafter, when the actuator MA continuously moves in the +X-axis direction, the first elastic part 1112 of the first input link 1110 and the second elastic part 1212 of the second input link 1210 may be contracted. As illustrated in FIG. 19, when the actuator MA moves in the +X-axis direction after the second contact, the length of the first input link 1110 may be reduced from about 42.8 mm. In addition, the length of the second input link 1210 may be reduced from about 45.5 mm.

In addition, when the actuator MA continuously moves in the +X-axis direction, the lengths of the first and second input links 1110 and 1210 may be contracted to rotate the third grasping link 1350 in the clockwise direction. Thus, the third grasping link 1350 may come in contact with a third contact point CT3 of the object Obj. As illustrated in FIG. 18, third contact may occur when the actuator MA moves by about 11.8 mm in the +X-axis direction, i.e., at the third contact point CT3 located at about −160 degrees.

According to the aforementioned embodiments of the inventive concepts, the first grasping link 1142 is in contact with the object Obj at the first contact point CT1, the second grasping link 1246 is in contact with the object Obj at the second contact point CT2, and the third grasping link 1350 is in contact with the object Obj at the third contact point CT3. Thus, the robotic driving mechanism 1000 may actively adapt to the outward shape of the object Obj to stably grasp the object Obj.

In addition, after the first grasping link 1142 is in contact with the object, the length of the first input link 1110 may be reduced to provide the additional degree of freedom. Thus, the second grasping link 1246 and the third grasping link 1350 may be additionally rotated to grasp the object. In addition, after the second grasping link 1246 is in contact with the object, the length of the second input link 1210 may be reduced to provide the additional degree of freedom. Thus, the third grasping link 1350 may be additionally rotated to grasp the object.

As a result, the degrees of freedom of the first to third link parts of the robotic driving mechanism according to the first embodiment may be more than the number of the actuator MA. In other words, even though the single actuator is used as described above, the first to third link parts may provide 3 degrees of freedom by the control of the variable lengths of the first and second input links.

The grasping motion according to the first embodiment of the inventive concepts was described above. Hereinafter, a method of driving a robotic driving mechanism according to the first embodiment of the inventive concepts will be described with reference to FIG. 20. The driving method according to the first embodiment may be realized by the robotic driving mechanism according to the first embodiment described with reference to FIGS. 9 to 19.

FIG. 20 is a flowchart illustrating a method of driving the robotic driving mechanism according to the first embodiment of the inventive concepts.

Referring to FIG. 20, the method of driving a robotic driving mechanism according to the first embodiment of the inventive concepts may include at least one of rotating a first link part and second and third link parts overlapping with the first link part together toward an object by providing driving force through an actuator (S100), grasping the object by a first grasping link of the first link part (S110), contracting a first input link, which is provided between the actuator and the first grasping link to input the driving force, when the first grasping link of the first link part grasps the object (S120), rotating a second grasping link of the second link part toward the object by the driving force of the actuator to grasp the object, while the first input link is contracted (S130), contracting a second input link, which is provided between the actuator and the second grasping link to input the driving force, when the second grasping link of the second link part grasps the object (S140), or rotating a third grasping link of the third link part toward the object by the driving force of the actuator to grasp the object, while the second input link is contracted (S150). Hereinafter, each of the steps will be described in detail.

In the step S100, the driving force may be provided through the actuator, and thus the first link part 1100 and the second and third link parts 1200 and 1300 overlapping with the first link part 1100 may be rotated together toward the object.

Since the actuator MA moves in the +X-axis direction, the first input link 1110 may push the first side link 1132, the second input link 1210 may push the (2-1)th side link 1232, and the third input link 1310 may push the (3-1)th side link 1332. Thus, the first grasping link 1142 of the first link part 1100, the second bottom link 1242 of the second link part 1200 and the (3-1)th bottom link 1342 of the third link part 1300 may be rotated together toward the object in the direction θ1.

In the step S110, the first grasping link 1142 may grasp the object. As described with reference to FIGS. 17 to 19, the first grasping link 1142 may grasp the object at the first contact point CT1.

Since the first link part 1100, the second link part 1200 and the third link part 1300 share the node, the second bottom link 1242 of the second link part 1200 and the (3-1)th bottom link 1342 of the third link part 1300 may also grasp the object at the first contact point CT1.

In the step S120, the first input link 1110 provided between the actuator MA and the first grasping link 1142 to input the driving force F may be contracted when the first grasping link 1142 of the first link part 1100 grasps the object.

In more detail, when the first grasping link 1142 grasps the object at the first contact point CT1, the first grasping link 1142 is no longer rotated even though the driving force F is provided through the actuator MA. Thus, when the driving force is provided through the actuator MA in the state where the first grasping link 1142 grasps the object, the length of the first elastic part 1112 of the first input link 1110 may be contracted.

In the step S130, the second grasping link 1246 of the second link part 1200 may be rotated toward the object by the driving force F of the actuator MA to grasp the object, while the first input link 1110 is contracted.

Since the second input link 1210 is provided with the additional degree of freedom when the first input link 1110 is contracted, the second grasping link 1246 may be additionally rotated toward the object. Thus, the second grasping link 1246 may grasp the object at the second contact point CT2.

At this time, since the second grasping link 1246 and the (3-2)th bottom link 1346 share the node, the (3-2)th bottom link 1346 of the third link part 1300 may also grasp the object at the second contact point CT2.

In an embodiment, the step S130 may be performed simultaneously with the step S120.

In the step S140, the second input link 1210 provided between the actuator MA and the second grasping link 1246 to input the driving force F may be contracted when the second grasping link 1246 of the second link part 1200 grasps the object.

In more detail, when the second grasping link 1246 grasps the object at the second contact point CT2, the second grasping link 1246 is no longer rotated even though the driving force F is provided through the actuator MA. Thus, when the driving force is provided through the actuator MA in the state where the second grasping link 1246 grasps the object, the length of the second elastic part 1212 of the second input link 1210 may be contracted. At this time, the length of the first elastic part 1112 of the first input link 1110 may also be contracted.

In the step S150, the third grasping link 1350 of the third link part 1300 may be rotated toward the object by the driving force F of the actuator MA to grasp the object, while the second input link 1210 is contracted.

Since the third input link 1310 is provided with the additional degree of freedom when the second input link 1210 and the first input link 1110 are contracted, the third grasping link 1350 may be additionally rotated toward the object. Thus, the third grasping link 1350 may grasp the object at the third contact point CT3.

In an embodiment, the step S150 may be performed simultaneously with the step S140.

The method of driving the robotic driving mechanism according to the first embodiment may adapt to various outward shapes of objects to stably grasp the objects. In other words, in the method of driving the robotic driving mechanism according to the first embodiment of the inventive concepts, the first grasping link, the second grasping link and the third grasping link may sequentially come in contact with the outward shape of the object, the second grasping link may be provided with the additional degree of freedom by the variable length of the first input link, and the third grasping link may be provided with the additional degree of freedom by the variable lengths of the first and second input links. Thus, it is possible to perform the grasping motion which can adapt to the outward shape of the object.

The robotic driving mechanism and the method of driving the same according to the first embodiment of the inventive concepts were described above. A robotic driving mechanism and a method of driving the same according to a second embodiment of the inventive concepts will be described hereinafter.

FIG. 21 is a schematic view illustrating a link of a robotic driving mechanism according to a second embodiment of the inventive concepts. The robotic driving mechanism 1000 according to the first embodiment includes three stacked link parts. However, a robotic driving mechanism 2000 according to the second embodiment may include two stacked link parts. In other words, the robotic driving mechanism 2000 according to the second embodiment may have two phalanx-shaped bars, unlike the robotic driving mechanism 1000 according to the first embodiment which has three phalanx-shaped bars.

Referring to FIG. 21, the robotic driving mechanism 2000 according to the second embodiment of the inventive concepts may include a first link part 2400 and a second link part 2500. Unless otherwise noted, the first and second link parts 2400 and 2500 may mean link parts of the robotic driving mechanism 2000 according to the second embodiment of the inventive concepts, hereinafter.

The first link part 2400 and the second link part 2500 may be stacked on each other and may receive driving force at a node A through an actuator (not shown) to perform bending, stretching and grasping motions. In an embodiment, ends of the first and second link parts 2400 and 2500 may be connected to the actuator via a connector.

Components and functions of the first link part 2400 according to the second embodiment may be the same as the components and the functions of the first link part 1100 according to the first embodiment described above, and thus detailed descriptions thereto are omitted.

The second link part 2500 according to the second embodiment of the inventive concepts may include a second input link 2510 which receives the driving force through the actuator and which has a constant length. In other words, the feature in which the second input link 2510 has the constant length in the second embodiment may be different from the feature in which the second input link 1210 has the variable length in the first embodiment.

Other components, e.g., a (2-1)th side link 2532, a (2-1)th top link 2534, a (2-2)th side link 2536, a (2-2)th top link 2538, a (2-3)th side link 2540 and a second bottom link 2542 of the second link part 2500 in the second embodiment except the second input link 2510 may have the same elements and functions as the (2-1)th side link 1232, the (2-1)th top link 1234, the (2-2)th side link 1236, the (2-2)th top link 1238, the (2-3)th side link 1240 and the second bottom link 1242 of the second link part 1200 according to the first embodiment, respectively, and thus detailed descriptions thereto are omitted.

In addition, a (2-3)th top link 2544 and a second grasping link 2546 of the second link part 2500 according to the second embodiment may have the same elements and functions as the (2-3)th top link 1244 and the second grasping link 1246 of the second link part 1200 according to the first embodiment, respectively, and thus detailed descriptions thereto are omitted.

FIG. 22 is a flowchart illustrating a method of driving the robotic driving mechanism according to the second embodiment of the inventive concepts.

Referring to FIG. 22, a method of driving a robotic driving mechanism according to the second embodiment of the inventive concepts may include at least one of rotating a first link part and a second link part overlapping with the first link part together toward an object by providing driving force through an actuator (S200), grasping the object by a first grasping link of the first link part (S210), contracting a first input link, which is provided between the actuator and the first grasping link to input the driving force, when the first grasping link of the first link part grasps the object (S220), or rotating a second grasping link of the second link part toward the object by the driving force of the actuator to grasp the object, while the first input link is contracted (S230).

In the step S200, the actuator may move in a +Xo-axis direction, and thus the first input link 2410 may push the first side link 2432 and the second input link 2510 may push the (2-1)th side link 2532. Thus, the first grasping link 2442 of the first link part 2400 and the second bottom link 2542 of the second link part 2500 may be rotated together toward the object in the direction θ1.

In the step S210, the first grasping link 2442 may grasp the object. As described with reference to FIGS. 17 to 19, the first grasping link 2442 may grasp the object at the first contact point CT1.

Since the first link part 2400 and the second link part 2500 share a node, the second bottom link 2542 of the second link part 2500 as well as the first grasping link 2442 may grasp the object at the first contact point CT1.

In the step S220, the first input link 2410 provided between the actuator and the first grasping link 2442 to input the driving force may be contracted when the first grasping link 2442 of the first link part 2400 grasps the object.

In more detail, when the first grasping link 2442 grasps the object at the first contact point CT1, the first grasping link 2442 is no longer rotated even though the driving force is provided through the actuator. Thus, when the driving force is provided through the actuator in the state where the first grasping link 2442 grasps the object, the length of the first elastic part 2412 of the first input link 2410 may be contracted.

In the step S230, the second grasping link 2546 of the second link part 2500 may be rotated toward the object by the driving force of the actuator to grasp the object, while the first input link 2410 is contracted.

Since the second input link 2510 is provided with an additional degree of freedom when the first input link 2410 is contracted, the second grasping link 2546 may be additionally rotated toward the object. Thus, the second grasping link 2546 may grasp the object at the second contact point CT2.

In an embodiment, the step S230 may be performed simultaneously with the step S220.

As a result, in the robotic driving mechanism and the method of driving the same according to the second embodiment of the inventive concepts, the first grasping link and the second grasping link may sequentially grasp the object and may sequentially come in contact with the outward shape of the object, and the second grasping link may be provided with the additional degree of freedom by the variable length of the first input link. Thus, it is possible to perform the grasping motion which can adapt to the outward shape of the object.

The robotic driving mechanisms and the methods of driving the same according to the embodiments of the inventive concepts may provide the degrees of freedom more than the number of the actuator, i.e., under-actuation, and thus the bending, stretching and grasping motions may be realized by a minimum actuator. As a result, a weight of the robotic driving mechanism may be reduced. In other words, the robotic driving mechanism according to some embodiments of the inventive concepts may be used as an end-effector, and thus difficulty of control by excessive actuators may be solved.

In addition, the embodiments of the inventive concepts may provide the additional degree of freedom by using the input link having the variable length, and thus the degree of freedom may be added by a simple method. As a result, the embodiments of the inventive concepts may be easily applied to a robot field.

Furthermore, the embodiments of the inventive concepts may provide the input link having the variable length by using an elastic body, and thus the robotic driving mechanism according to the embodiments may stably grasp various-shaped objects.

The robotic driving mechanism according to the first embodiment may include the first to third link parts, and the robotic driving mechanism according to the second embodiment may include the first and second link parts. However, embodiments of the inventive concepts are not limited thereto. In other embodiments, the robotic driving mechanism may include four or more link parts.

The embodiments of the inventive concepts may be applied to a hand of a humanoid robot performing a similar motion to a human motion and/or end-effectors of various robot arms. In other words, the robotic driving mechanism and the method of driving the same according to the embodiments of the inventive concepts may be applied to a bionic prosthesis industry, service/manufacturing equipment, and medical robots.

The robotic finger prosthesis according to embodiments of the inventive concepts may perform the bending or stretching motion by using the proximal phalanx portion of the user having the cut finger. In addition, since the robotic finger prosthesis adapts to various-shaped objects, the contact area between the robotic finger prosthesis and the object may be increased to stably perform the grasping motion.

The robotic driving mechanism according to an embodiment of the inventive concepts may include a first link part, a second link part, and a third link part. The first link part may include: a first input link receiving driving force through an actuator and including a first elastic part having a length controlled according to a motion of grasping an object; and a first grasping link rotated by movement of the first input link to grasp the object. The second link part may include: a second input link receiving the driving force through the actuator at the same time and including a second elastic part having a length controlled according to the motion of grasping the object; and a second grasping link rotated by movement of the second input link to grasp the object. The third link part may include: a third input link receiving the driving force through the actuator at the same time and having a constant length; and a third grasping link rotated by movement of the third input link to grasp the object.

According to an embodiment of the inventive concepts, the first, second and third input links may be provided together with the driving force by the actuator. For example, the first, second and third input links may be driven by a single actuator.

In addition, according to an embodiment of the inventive concepts, the lengths of the first and second input links may be variable by the elastic parts. Thus, when the driving force is continuously provided to the first input link through the actuator in the state where the first grasping link of the first link part grasps the object, the first elastic part may be contracted. In addition, when the driving force is continuously provided to the second input link through the actuator in the state where the second grasping link of the second link part grasps the object, the second elastic part may be contracted. Furthermore, the second grasping link of the second link part may be rotated to grasp the object when the first elastic part is contracted, and the third grasping link of the third link part may be rotated to grasp the object when the first and second elastic parts are contracted.

In other words, when the first grasping link grasps the object, the length of the first input link may be shortened to provide the degrees of freedom to the second and third grasping links in such a way that the second and third grasping links grasp the object. In addition, when the second grasping link grasps the object by the additional rotation, the length of the second input link may be shortened to provide an additional degree of freedom to the third grasping link in such a way that the third grasping link grasps the object. Thus, according to an embodiment of the inventive concepts, the degrees of freedom more than the number of the actuator may be provided by the elastic part included in the input link. As a result, the robotic driving mechanism and the method of driving the same according to embodiments of the inventive concepts may adapt to various shapes of objects to stably grasp the objects.

While the inventive concepts have been described with reference to exemplary embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. An adaptive robotic finger prosthesis for grasping an arbitrary object shape, comprising:
    a proximal phalanx body configured to be worn on a proximal phalanx portion of a cut finger;
    a middle phalanx body connected, to the proximal phalanx body and configured to function as a middle phalanx portion of the cut finger;
    a distal phalanx body connected to the middle phalanx body and configured to function as a distal phalanx portion of the cut finger;
    a first proximal phalanx link disposed under the proximal phalanx body;
    a second proximal phalanx link disposed on the proximal phalanx body and connected to the first proximal phalanx link; and
    a proximal phalanx elastic member provided at a joint between the first proximal phalanx link and the second proximal phalanx link to provide elastic force.

2. The adaptive robotic finger prosthesis of claim 1, wherein an angle between the first proximal phalanx link and the second proximal phalanx link increases as the first proximal phalanx link comes in contact with an object and is pressed, in a motion of grasping the object.

3. The adaptive robotic finger prosthesis of claim 1, wherein the second proximal phalanx link applies force to the middle phalanx body to fold the middle phalanx body and the distal phalanx body inward as the first proximal phalanx link comes in contact with an object and is pressed, in a motion of grasping the object.

4. The adaptive robotic finger prosthesis of claim 1, wherein an angle between the first proximal phalanx link and the second proximal phalanx link is fixed by the proximal phalanx elastic member in a bending or stretching motion performed in the absence of contact with an object.

5. The adaptive robotic finger prosthesis of claim 4, wherein a mechanical angle limiting element for limiting the angle between the first and second proximal phalanx links is provided at one of the first proximal phalanx link and the second proximal phalanx link, such that the angle between the first and second proximal phalanx links is fixed to an angle of the mechanical angle limiting element by the proximal phalanx elastic member in the bending or stretching motion.

6. The adaptive robotic finger prosthesis of claim 1, further comprising:
    a first middle phalanx link which is disposed under the middle phalanx body and of which one end portion is connected to the proximal phalanx body;
    a second middle phalanx link of which one end portion is connected to another end portion of the first middle phalanx link and of which another end portion is connected to the distal phalanx body;
    a third middle phalanx link which is disposed on the middle phalanx body and which interconnects the proximal phalanx body and the distal phalanx body; and
    a middle phalanx elastic member provided at a joint between the first and second middle phalanx links to provide elastic force.

7. The adaptive robotic finger prosthesis of claim 6, wherein an angle between the first middle phalanx link and the second middle phalanx link increases as the first middle phalanx link comes in contact with an object and is pressed, in a motion of grasping the object.

8. The adaptive robotic finger prosthesis of claim 6, wherein the second middle phalanx link applies force to the distal phalanx, body to fold the distal phalanx body inward as the first middle phalanx link comes in contact with an object and is pressed, in a motion of grasping the object.

9. The adaptive robotic finger prosthesis of claim 6, wherein an angle between the first middle phalanx link and the second middle phalanx link is fixed by the middle phalanx elastic member in a bending or stretching motion performed in the absence of contact with an object.

10. The adaptive robotic finger prosthesis of claim 9, wherein a mechanical angle limiting element for limiting the angle between the first and second middle phalanx links is provided at one of the first middle phalanx link and the second middle phalanx link, such that the angle between the first and second middle phalanx links is fixed to an angle of the mechanical angle limiting element by the middle phalanx elastic member in the bending or stretching motion.

11. The adaptive robotic finger prosthesis of claim 1, further comprising:
    a palm fixing part configured to be fixed at a palm of a user,
    wherein the palm fixing part is connected to each of the proximal phalanx body and the first proximal phalanx link.

12. The adaptive robotic finger prosthesis of claim 11, further comprising:

a connection bracket which joint-connects the palm fixing part to the proximal phalanx body or the first proximal phalanx link, wherein the palm fixing part is configured to be rotated inward and outward with respect to the proximal phalanx body or the first proximal phalanx link by the connection bracket.

\* \* \* \* \*